(12) United States Patent
Cao et al.

(10) Patent No.: US 6,916,477 B2
(45) Date of Patent: Jul. 12, 2005

(54) ATTENUATED FORMS OF BOVINE VIRAL DIARRHEA VIRUS

(75) Inventors: Xuemei Cao, East Lyme, CT (US); Michael G. Sheppard, Stonington, CT (US)

(73) Assignee: Pfizer Inc., New York, NY (US)

( * ) Notice: Subject to any disclaimer, the term of this patent is extended or adjusted under 35 U.S.C. 154(b) by 219 days.

(21) Appl. No.: 10/134,288

(22) Filed: Apr. 29, 2002

(65) Prior Publication Data

US 2003/0165520 A1 Sep. 4, 2003

Related U.S. Application Data

(62) Division of application No. 09/702,330, filed on Oct. 31, 2000, now Pat. No. 6,410,032, which is a division of application No. 09/433,262, filed on Nov. 4, 1999, now Pat. No. 6,168,942.
(60) Provisional application No. 60/107,908, filed on Nov. 10, 1998.

(51) Int. Cl.$^7$ .................. A61K 39/12; A01N 63/00
(52) U.S. Cl. ................ 424/218.1; 424/93.2; 435/235.1; 435/320.1; 435/91.1; 435/440; 435/455; 435/325; 536/23.1
(58) Field of Search .................. 435/235.1, 320.1, 435/91.1, 325, 440, 455; 536/23.1; 424/93.2, 218.1

(56) References Cited

U.S. PATENT DOCUMENTS 5,206,163 A 4/1993 Renard et al.

FOREIGN PATENT DOCUMENTS

JP 62-69991 3/1987

OTHER PUBLICATIONS

Kupfermann, et al. Journal of Virology, 1996, vol. 70, No. 11, pp. 8175–8181.*
Collett, Marc S., et al., Proteins Encoded by Bovine Viral Diarrhea Virus: The Genomic Organization of a Pestivirus, *Virology*, 165, 200–208 (1988).
Vassilev, Ventzislav B., et al., Authentic and Chimeric Full–Length Genomic cDNA Clones of Bovine Viral Diarrhea Virus that Yield Infectious Transcripts, *Journal of Virology*, vol. 71, No. 1, 471–478 (1997).

* cited by examiner

*Primary Examiner*—Gerry Leffers
(74) *Attorney, Agent, or Firm*—Thomas A. Wootton; Kenneth I. Kohn; Kohn & Associates, PLLC

(57) ABSTRACT

The present invention is directed to a method of producing attenuated forms of bovine viral diarrhea (BVD) virus by mutating the $N^{pro}$ protease gene. The invention includes the attenuated viruses made by this method, antibodies generated using these viruses, and vaccines that can be used for immunizing cattle.

11 Claims, 25 Drawing Sheets

```
CACGCGTATCGATGAATTCGTTAATACGACTCACTATAGTATACGAGAATTAGAAAAGGCACTCGTATAC
|----+----|----+----|----+----|----+----|----+----|----+----|----+----| 70
GTGCGCATAGCTACTTAAGCAATTATGCTGAGTGATATCATATGCTCTTAATCTTTTCCGTGAGCATATG

GTATTGGGCAATTAAAAATAATAATTAGGCCTAGGGAACAAATCCCTCTCAGCGAAGGCCGAAAAGAGGC
|----+----|----+----|----+----|----+----|----+----|----+----|----+----| 140
CATAACCCGTTAATTTTTATTATTAATCCGGATCCCTTGTTTAGGGAGAGTCGCTTCCGGCTTTTCTCCG

TAGCCATGCCCTTAGTAGGACTAGCATAATGAGGGGGGTAGCAACAGTGGTGAGTTCGTTGGATGGCTTA
|----+----|----+----|----+----|----+----|----+----|----+----|----+----| 210
ATCGGTACGGGAATCATCCTGATCGTATTACTCCCCCCATCGTTGTCACCACTCAAGCAACCTACCGAAT

AGCCCTGAGTACAGGGTAGTCGTCAGTGGTTCGACGCCTTGGAATAAAGGTCTCGAGATGCCACGTGGAC
|----+----|----+----|----+----|----+----|----+----|----+----|----+----| 280
TCGGGACTCATGTCCCATCAGCAGTCACCAAGCTGCGGAACCTTATTTCCAGAGCTCTACGGTGCACCTG

GAGGGCATGCCCAAAGCACATCTTAACCTGAGCGGGGGTCGCCCAGGTAAAAGCAGTTTTAACCGACTGT
|----+----|----+----|----+----|----+----|----+----|----+----|----+----| 350
CTCCCGTACGGGTTTCGTGTAGAATTGGACTCGCCCCCAGCGGGTCCATTTTCGTCAAAATTGGCTGACA

TACGAATACAGCCTGATAGGGTGCTGCAGAGGCCCACTGTATTGCTACTAAAAATCTCTGCTGTACATGG
|----+----|----+----|----+----|----+----|----+----|----+----|----+----| 420
ATGCTTATGTCGGACTATCCCACGACGTCTCCGGGTGACATAACGATGATTTTTAGAGACGACATGTACC

CACATGTCAGACACGAAAGAAGAGGGAGCAACAAAAAAGAAAACACAGAAACCCGACAGACTAGAAAGGG
|----+----|----+----|----+----|----+----|----+----|----+----|----+----| 490
GTGTACAGTCTGTGCTTTCTTCTCCCTCGTTGTTTTTTCTTTTGTGTCTTTGGGCTGTCTGATCTTTCCC

GGAAAATGAAAATAGTGCCCAAAGAATCTGAAAAAGACAGCAAAACTAAACCTCCGGATGCTACAATAGT
|----+----|----+----|----+----|----+----|----+----|----+----|----+----| 560
CCTTTTACTTTTATCACGGGTTTCTTAGACTTTTTCTGTCGTTTTGATTTGGAGGCCTACGATGTTATCA

GGTGGAAGGAGTCAAATACCAGGTGAGGAAGAAGGGAAAAACCAAGAGTAAAAACACTCAGGACGGCTTG
|----+----|----+----|----+----|----+----|----+----|----+----|----+----| 630
CCACCTTCCTCAGTTTATGGTCCACTCCTTCTTCCCTTTTTGGTTCTCATTTTTGTGAGTCCTGCCGAAC
```

FIG. 2A

```
TACCATAACAAAAACAAACCTCAGGAATCACGCAAGAAACTGGAAAAAGCATTGTTGGCGTGGGCAATAA
                                                                              700
ATGGTATTGTTTTTGTTTGGAGTCCTTAGTGCGTTCTTTGACCTTTTTCGTAACAACCGCACCCGTTATT

TAGCTATAGTTTTGTTTCAAGTTACAATGGGAGAAAACATAACACAGTGGAACCTACAAGATAATGGGAC
                                                                              770
ATCGATATCAAAACAAAGTTCAATGTTACCCTCTTTTGTATTGTGTCACCTTGGATGTTCTATTACCCTG

GGAAGGGATACAACGGGCAATGTTCCAAAGGGGTGTGAATAGAAGTTTACATGGAATCTGGCCAGAGAAA
                                                                              840
CCTTCCCTATGTTGCCCGTTACAAGGTTTCCCCACACTTATCTTCAAATGTACCTTAGACCGGTCTCTTT

ATCTGTACTGGCGTCCCTTCCCATCTAGCCACCGATATAGAACTAAAAACAATTCATGGTATGATGGATG
                                                                              910
TAGACATGACCGCAGGGAAGGGTAGATCGGTGGCTATATCTTGATTTTTGTTAAGTACCATACTACCTAC

CAAGTGAGAAGACCAACTACACGTGTTGCAGACTTCAACGCCATGAGTGGAACAAGCATGGTTGGTGCAA
                                                                              980
GTTCACTCTTCTGGTTGATGTGCACAACGTCTGAAGTTGCGGTACTCACCTTGTTCGTACCAACCACGTT

CTGGTACAATATTGAACCCTGGATTCTAGTCATGAATAGAACCCAAGCCAATCTCACTGAGGGACAACCA
                                                                              1050
GACCATGTTATAACTTGGGACCTAAGATCAGTACTTATCTTGGGTTCGGTTAGAGTGACTCCCTGTTGGT

CCAAGGGAGTGCGCAGTCACTTGTAGGTATGATAGGGCTAGTGACTTAAACGTGGTAACACAAGCTAGAG
                                                                              1120
GGTTCCCTCACGCGTCAGTGAACATCCATACTATCCCGATCACTGAATTTGCACCATTGTGTTCGATCTC

ATAGCCCCACACCCTTAACAGGTTGCAAGAAAGGAAAGAACTTCTCCTTTGCAGGCATATTGATGCGGGG
                                                                              1190
TATCGGGGTGTGGGAATTGTCCAACGTTCTTTCCTTTCTTGAAGAGGAAACGTCCGTATAACTACGCCCC

CCCCTGCAACTTTGAAATAGCTGCAAGTGATGTATTATTCAAAGAACATGAACGCATTAGTATGTTCCAG
                                                                              1260
GGGGACGTTGAAACTTTATCGACGTTCACTACATAATAAGTTTCTTGTACTTGCGTAATCATACAAGGTC
```

FIG. 2B

```
GATACCACTCTTTACCTTGTTGACGGGTTGACCAACTCCTTAGAAGGTGCCAGACAAGGAACCGCTAAAC
----+----+----+----+----+----+----+----+----+----+----+----+----+----+ 1330
CTATGGTGAGAAATGGAACAACTGCCCAACTGGTTGAGGAATCTTCCACGGTCTGTTCCTTGGCGATTTG

TGACAACCTGGTTAGGCAAGCAGCTCGGGATACTAGGAAAAAAGTTGGAAAACAAGAGTAAGACGTGGTT
----+----+----+----+----+----+----+----+----+----+----+----+----+----+ 1400
ACTGTTGGACCAATCCGTTCGTCGAGCCCTATGATCCTTTTTTCAACCTTTTGTTCTCATTCTGCACCAA

TGGAGCATACGCTGCTTCCCCTTACTGTGATGTCGATCGCAAAATTGGCTACATATGGTATACAAAAAAT
----+----+----+----+----+----+----+----+----+----+----+----+----+----+ 1470
ACCTCGTATGCGACGAAGGGGAATGACACTACAGCTAGCGTTTTAACCGATGTATACCATATGTTTTTTA

TGCACCCCTGCCTGCTTACCCAAGAACACAAAAATTGTCGGCCCTGGGAAATTTGGCACCAATGCAGAGG
----+----+----+----+----+----+----+----+----+----+----+----+----+----+ 1540
ACGTGGGGACGGACGAATGGGTTCTTGTGTTTTTAACAGCCGGGACCCTTTAAACCGTGGTTACGTCTCC

ACGGCAAGATATTACATGAGATGGGGGGTCACTTGTCGGAGGTACTACTACTTTCTTTAGTGGTGCTGTC
----+----+----+----+----+----+----+----+----+----+----+----+----+----+ 1610
TGCCGTTCTATAATGTACTCTACCCCCAGTGAACAGCCTCCATGATGATGAAAGAAATCACCACGACAG

CGACTTCGCACCGGAAACAGCTAGTGTAATGTACCTAATCCTACATTTTTCCATCCCACAAAGTCACGTT
----+----+----+----+----+----+----+----+----+----+----+----+----+----+ 1680
GCTGAAGCGTGGCCTTTGTCGATCACATTACATGGATTAGGATGTAAAAAGGTAGGGTGTTTCAGTGCAA

GATGTAATGGATTGTGATAAGACCCAGTTGAACCTCACAGTGGAGCTGACAACAGCTGAAGTAATACCAG
----+----+----+----+----+----+----+----+----+----+----+----+----+----+ 1750
CTACATTACCTAACACTATTCTGGGTCAACTTGGAGTGTCACCTCGACTGTTGTCGACTTCATTATGGTC

GGTCGGTCTGGAATCTAGGCAAATATGTATGTATAAGACCAAATTGGTGGCCTTATGAGACAACTGTAGT
----+----+----+----+----+----+----+----+----+----+----+----+----+----+ 1820
CCAGCCAGACCTTAGATCCGTTTATACATACATATTCTGGTTTAACCACCGGAATACTCTGTTGACATCA

GTTGGCATTTGAAGAGGTGAGCCAGGTGGTGAAGTTAGTGTTGAGGGCACTCAGAGATTTAACACGCATT
----+----+----+----+----+----+----+----+----+----+----+----+----+----+ 1890
CAACCGTAAACTTCTCCACTCGGTCCACCACTTCAATCACAACTCCCGTGAGTCTCTAAATTGTGCGTAA
```

FIG. 2C

```
TGGAACGCTGCAACAACTACTGCTTTTTTAGTATGCCTTGTTAAGATAGTCAGGGGGCCAGATGGTACAG
----+----+----+----+----+----+----+----+----+----+----+----+----+---- 1960
ACCTTGCGACGTTGTTGATGACGAAAAAATCATACGGAACAATTCTATCAGTCCCCCGGTCTACCATGTC

GGCATTCTGTGGCTACTATTGATAACAGGGGTACAAGGGCACTTGGATTGCAAACCTGAATTCTCGTATG
----+----+----+----+----+----+----+----+----+----+----+----+----+---- 2030
CCGTAAGACACCGATGATAACTATTGTCCCCATGTTCCCGTGAACCTAACGTTTGGACTTAAGAGCATAC

CCATAGCAAAGGACGAAAGAATTGGTCAACTGGGGGCTGAAGGCCTTACCACCACTTGGAAGGAATACTC
----+----+----+----+----+----+----+----+----+----+----+----+----+---- 2100
GGTATCGTTTCCTGCTTTCTTAACCAGTTGACCCCCGACTTCCGGAATGGTGGTGAACCTTCCTTATGAG

ACCTGGAATGAAGCTGGAAGACACAATGGTCATTGCTTGGTGCGAAGATGGGAAGTTAATGTACCTCCAA
----+----+----+----+----+----+----+----+----+----+----+----+----+---- 2170
TGGACCTTACTTCGACCTTCTGTGTTACCAGTAACGAACCACGCTTCTACCCTTCAATTACATGGAGGTT

AGATGCACGAGAGAAACCAGATATCTCGCAATCTTGCATACAAGAGCCTTGCCGACCAGTGTGGTATTCA
----+----+----+----+----+----+----+----+----+----+----+----+----+---- 2240
TCTACGTGCTCTCTTTGGTCTATAGAGCGTTAGAACGTATGTTCTCGGAACGGCTGGTCACACCATAAGT

AAAAACTCTTTGATGGGCGAAAGCAAGAGGATGTAGTCGAAATGAACGACAACTTTGAATTTGGACTCTG
----+----+----+----+----+----+----+----+----+----+----+----+----+---- 2310
TTTTTGAGAAACTACCCGCTTTCGTTCTCCTACATCAGCTTTACTTGCTGTTGAAACTTAAACCTGAGAC

CCCATGTGATGCCAAACCCATAGTAAGAGGGAAGTTCAATACAACGCTGCTGAACGGACCGGCCTTCCAG
----+----+----+----+----+----+----+----+----+----+----+----+----+---- 2380
GGGTACACTACGGTTTGGGTATCATTCTCCCTTCAAGTTATGTTGCGACGACTTGCCTGGCCGGAAGGTC

ATGGTATGCCCCATAGGATGGACAGGGACTGTAAGCTGTACGTCATTCAATATGGACACCTTAGCCACAA
----+----+----+----+----+----+----+----+----+----+----+----+----+---- 2450
TACCATACGGGGTATCCTACCTGTCCCTGACATTCGACATGCAGTAAGTTATACCTGTGGAATCGGTGTT

CTGTGGTACGGACATATAGAAGGTCTAAACCATTCCCTCATAGGCAAGGCTGTATCACCCAAAAGAATCT
----+----+----+----+----+----+----+----+----+----+----+----+----+---- 2520
GACACCATGCCTGTATATCTTCCAGATTTGGTAAGGGAGTATCCGTTCCGACATAGTGGGTTTTCTTAGA
```

FIG. 2D

```
GGGGGAGGATCTCCATAACTGCATCCTTGGAGGAAATTGGACTTGTGTGCCTGGAGACCAACTACTATAC
─┼──┼──┼──┼──┼──┼──┼──┼──┼──┼──┼──┼──┼──+ 2590
CCCCCTCCTAGAGGTATTGACGTAGGAACCTCCTTTAACCTGAACACACGGACCTCTGGTTGATGATATG

AAAGGGGCTCTATTGAATCTTGCAAGTGGTGTGGCTATCAATTTAAAGAGAGTGAGGGACTACCACACT
─┼──┼──┼──┼──┼──┼──┼──┼──┼──┼──┼──┼──┼──+ 2660
TTTCCCCCGAGATAACTTAGAACGTTCACCACACCGATAGTTAAATTTCTCTCACTCCCTGATGGTGTGA

ACCCCATTGGCAAGTGTAAATTGGAGAACGAGACTGGTTACAGGCTAGTAGACAGTACCTCTTGCAATAG
─┼──┼──┼──┼──┼──┼──┼──┼──┼──┼──┼──┼──┼──+ 2730
TGGGGTAACCGTTCACATTTAACCTCTTGCTCTGACCAATGTCCGATCATCTGTCATGGAGAACGTTATC

AGAAGGTGTGGCCATAGTACCACAAGGGACATTAAAGTGCAAGATAGGAAAAACAACTGTACAGGTCATA
─┼──┼──┼──┼──┼──┼──┼──┼──┼──┼──┼──┼──┼──+ 2800
TCTTCCACACCGGTATCATGGTGTTCCCTGTAATTTCACGTTCTATCCTTTTTGTTGACATGTCCAGTAT

GCTATGGATACCAAACTCGGACCTATGCCTTGCAGACCATATGAAATCATATCAAGTGAGGGGCCTGTAG
─┼──┼──┼──┼──┼──┼──┼──┼──┼──┼──┼──┼──┼──+ 2870
CGATACCTATGGTTTGAGCCTGGATACGGAACGTCTGGTATACTTTAGTATAGTTCACTCCCCGGACATC

AAAAGACAGCGTGTACTTTCAACTACACTAAGACATTAAAAAATAAGTATTTTGAGCCCAGAGACAGCTA
─┼──┼──┼──┼──┼──┼──┼──┼──┼──┼──┼──┼──┼──+ 2940
TTTTCTGTCGCACATGAAAGTTGATGTGATTCTGTAATTTTTTATTCATAAAACTCGGGTCTCTGTCGAT

CTTTCAGCAATACATGCTAAAAGGAGAGTATCAATACTGGTTTGACCTGGAGGTGACTGACCATCACCGG
─┼──┼──┼──┼──┼──┼──┼──┼──┼──┼──┼──┼──┼──+ 3010
GAAAGTCGTTATGTACGATTTTCCTCTCATAGTTATGACCAAACTGGACCTCCACTGACTGGTAGTGGCC

GATTACTTCGCTGAGTCCATATTAGTGGTGGTAGTAGCCCTCTTGGGTGGCAGATATGTACTTTCGTTAC
─┼──┼──┼──┼──┼──┼──┼──┼──┼──┼──┼──┼──┼──+ 3080
CTAATGAAGCGACTCAGGTATAATCACCACCATCATCGGGAGAACCCACCGTCTATACATGAAACCAATG

TGGTTACATACATGGTCTTATCAGAACAGAAGGCCTTAGGGATTCAGTATGGATCAGGGGAAGTGGTGAT
─┼──┼──┼──┼──┼──┼──┼──┼──┼──┼──┼──┼──┼──+ 3150
ACCAATGTATGTACCAGAATAGTCTTGTCTTCCGGAATCCCTAAGTCATACCTAGTCCCCTTCACCACTA
```

FIG. 2E

```
GATGGGCAACTTGCTAACCCATAACAATATTGAAGTGGTGACATACTTCTTGCTGCTGTACCTACTGCTG
----+----+----+----+----+----+----+----+----+----+----+----+----+---- 3220
CTACCCGTTGAACGATTGGGTATTGTTATAACTTCACCACTGTATGAAGAACGACGACATGGATGACGAC

AGGGAGGAGAGCGTAAAGAAGTGGGTCTTACTCTTATACCACATCTTAGTGGTACACCCAATCAAATCTG
----+----+----+----+----+----+----+----+----+----+----+----+----+---- 3290
TCCCTCCTCTCGCATTTCTTCACCCAGAATGAGAATATGGTGTAGAATCACCATGTGGGTTAGTTTAGAC

TAATTGTGATCCTACTGATGATTGGGGATGTGGTAAAGGCCGATTCAGGGGGCCAAGAGTACTTGGGGAA
----+----+----+----+----+----+----+----+----+----+----+----+----+---- 3360
ATTAACACTAGGATGACTACTAACCCCTACACCATTTCCGGCTAAGTCCCCCGGTTCTCATGAACCCCTT

AATAGACCTCTGTTTTACAACAGTAGTACTAATCGTCATAGGTTTAATCATAGCTAGGCGTGACCCAACT
----+----+----+----+----+----+----+----+----+----+----+----+----+---- 3430
TTATCTGGAGACAAAATGTTGTCATCATGATTAGCAGTATCCAAATTAGTATCGATCCGCACTGGGTTGA

ATAGTGCCACTGGTAACAATAATGGCAGCACTGAGGGTCACTGAACTGACCCACCAGCCTGGAGTTGACA
----+----+----+----+----+----+----+----+----+----+----+----+----+---- 3500
TATCACGGTGACCATTGTTATTACCGTCGTGACTCCCAGTGACTTGACTGGGTGGTCGGACCTCAACTGT

TCGCTGTGGCGGTCATGACTATAACCCTACTGATGGTTAGCTATGTGACAGATTATTTTAGATATAAAAA
----+----+----+----+----+----+----+----+----+----+----+----+----+---- 3570
AGCGACACCGCCAGTACTGATATTGGGATGACTACCAATCGATACACTGTCTAATAAAATCTATATTTTT

ATGGTTACAGTGCATTCTCAGCCTGGTATCTGCGGTGTTCTTGATAAGAAGCCTAATATACCTAGGTAGA
----+----+----+----+----+----+----+----+----+----+----+----+----+---- 3640
TACCAATGTCACGTAAGAGTCGGACCATAGACGCCACAAGAACTATTCTTCGGATTATATGGATCCATCT

ATCGAGATGCCAGAGGTAACTATCCCAAACTGGAGACCACTAACTTTAATACTATTATATTTGATCTCAA
----+----+----+----+----+----+----+----+----+----+----+----+----+---- 3710
TAGCTCTACGGTCTCCATTGATAGGGTTTGACCTCTGGTGATTGAAATTATGATAATATAAACTAGAGTT

CAACAATTGTAACGAGGTGGAAGGTTGACGTGGCTGGCCTATTGTTGCAATGTGTGCCTATCTTATTGCT
----+----+----+----+----+----+----+----+----+----+----+----+----+---- 3780
GTTGTTAACATTGCTCCACCTTCCAACTGCACCGACCGGATAACAACGTTACACACGGATAGAATAACGA
```

FIG. 2F

```
GGTCACAACCTTGTGGGCCGACTTCTTAACCCTAATACTGATCCTGCCTACCTATGAATTGGTTAAATTA
                                                                      3850
CCAGTGTTGGAACACCCGGCTGAAGAATTGGGATTATGACTAGGACGGATGGATACTTAACCAATTTAAT

TACTATCTGAAAACTGTTAGGACTGATACAGAAGAAGTTGGCTAGGGGGATAGACTATACAAGAGTTG
                                                                      3920
ATGATAGACTTTTGACAATCCTGACTATGTCTTTCTTCAACCGATCCCCCCTATCTGATATGTTCTCAAC

ACTCCATCTACGACGTTGATGAGAGTGGAGAGGGCGTATATCTTTTTCCATCAAGGCAGAAAGCACAGGG
                                                                      3990
TGAGGTAGATGCTGCAACTACTCTCACCTCTCCCGCATATAGAAAAAGGTAGTTCCGTCTTTCGTGTCCC

GAATTTTTCTATACTCTTGCCCCTTATCAAAGCAACACTGATAAGTTGCGTCAGCAGTAAATGGCAGCTA
                                                                      4060
CTTAAAAAGATATGAGAACGGGGAATAGTTTCGTTGTGACTATTCAACGCAGTCGTCATTTACCGTCGAT

ATATACATGAGTTACTTAACTTTGGACTTTATGTACTACATGCACAGGAAAGTTATAGAAGAGATCTCAG
                                                                      4130
TATATGTACTCAATGAATTGAAACCTGAAATACATGATGTACGTGTCCTTTCAATATCTTCTCTAGAGTC

GAGGTACCAACATAATATCCAGGTTAGTGGCAGCACTCATAGAGCTGAACTGGTCCATGGAAGAAGAGGA
                                                                      4200
CTCCATGGTTGTATTATAGGTCCAATCACCGTCGTGAGTATCTCGACTTGACCAGGTACCTTCTTCTCCT

GAGCAAAGGCTTAAAGAAGTTTTATCTATTGTCTGGAAGGTTGAGAAACCTAATAATAAAACATAAGGTA
                                                                      4270
CTCGTTTCCGAATTTCTTCAAAATAGATAACAGACCTTCCAACTCTTTGGATTATTATTTTGTATTCCAT

AGGAATGAGACCGTGGCTTCTTGGTACGGGGAGGAGGAAGTCTACGGTATGCCAAAGATCATGACTATAA
                                                                      4340
TCCTTACTCTGGCACCGAAGAACCATGCCCCTCCTCCTTCAGATGCCATACGGTTTCTAGTACTGATATT

TCAAGGCCAGTACACTGAGTAAGAGCAGGCACTGCATAATATGCACTGTATGTGAGGGCCGAGAGTGGAA
                                                                      4410
AGTTCCGGTCATGTGACTCATTCTCGTCCGTGACGTATTATACGTGACATACACTCCCGGCTCTCACCTT
```

FIG. 2G

```
AGGTGGCACCTGCCCAAAATGTGGACGCCATGGGAAGCCGATAACGTGTGGGATGTCGCTAGCAGATTTT
————+————+————+————+————+————+————+————+————+————+————+————+————+ 4480
TCCACCGTGGACGGGTTTTACACCTGCGGTACCCTTCGGCTATTGCACACCCTACAGCGATCGTCTAAAA

GAAGAAAGACACTATAAAAGAATCTTTATAAGGGAAGGCAACTTTGAGGGTATGTGCAGCCGATGCCAGG
————+————+————+————+————+————+————+————+————+————+————+————+————+ 4550
CTTCTTTCTGTGATATTTTCTTAGAAATATTCCCTTCCGTTGAAACTCCCATACACGTCGGCTACGGTCC

GAAAGCATAGGAGGTTTGAAATGGACCGGGAACCTAAGAGTGCCAGATACTGTGCTGAGTGTAATAGGCT
————+————+————+————+————+————+————+————+————+————+————+————+————+ 4620
CTTTCGTATCCTCCAAACTTTACCTGGCCCTTGGATTCTCACGGTCTATGACACGACTCACATTATCCGA

GCATCCTGCTGAGGAAGGTGACTTTTGGGCAGAGTCGAGCATGTTGGGCCTCAAAATCACCTACTTTGCG
————+————+————+————+————+————+————+————+————+————+————+————+————+ 4690
CGTAGGACGACTCCTTCCACTGAAAACCCGTCTCAGCTCGTACAACCCGGAGTTTTAGTGGATGAAACGC

CTGATGGATGGAAAGGTGTATGATATCACAGAGTGGGCTGGATGCCAGCGTGTGGGAATCTCCCCAGATA
————+————+————+————+————+————+————+————+————+————+————+————+————+ 4760
GACTACCTACCTTTCCACATACTATAGTGTCTCACCCGACCTACGGTCGCACACCCTTAGAGGGGTCTAT

CCCACAGAGTCCCTTGTCACATCTCATTTGGTTCACGGATGCCTTTCAGGCAGGAATACAATGGCTTTGT
————+————+————+————+————+————+————+————+————+————+————+————+————+ 4830
GGGTGTCTCAGGGAACAGTGTAGAGTAAACCAAGTGCCTACGGAAAGTCCGTCCTTATGTTACCGAAACA

ACAATATACCGCTAGGGGGCAACTATTTCTGAGAAACTTGCCCGTACTGGCAACTAAAGTAAAAATGCTC
————+————+————+————+————+————+————+————+————+————+————+————+————+ 4900
TGTTATATGGCGATCCCCCGTTGATAAAGACTCTTTGAACGGGCATGACCGTTGATTTCATTTTTACGAG

ATGGTAGGCAACCTTGGAGAAGAAATTGGTAATCTGGAACATCTTGGGTGGATCCTAAGGGGGCCTGCCG
————+————+————+————+————+————+————+————+————+————+————+————+————+ 4970
TACCATCCGTTGGAACCTCTTCTTTAACCATTAGACCTTGTAGAACCCACCTAGGATTCCCCCGGACGGC

TGTGTAAGAAGATCACAGAGCACGAAAAATGCCACATTAATATACTGGATAAACTAACCGCATTTTTCGG
————+————+————+————+————+————+————+————+————+————+————+————+————+ 5040
ACACATTCTTCTAGTGTCTCGTGCTTTTTACGGTGTAATTATATGACCTATTTGATTGGCGTAAAAAGCC
```

FIG. 2H

```
GATCATGCCAAGGGGGACTACACCCAGAGCCCCGGTGAGGTTCCCTACGAGCTTACTAAAAGTGAGGAGG
─────┼─────┼─────┼─────┼─────┼─────┼─────┼─────┼─────┼─────┼─────┼─────┼─────┼── 5110
CTAGTACGGTTCCCCCTGATGTGGGTCTCGGGGCCACTCCAAGGGATGCTCGAATGATTTTCACTCCTCC

GGTCTGGAGACTGCCTGGGCTTACACACACCAAGGCGGGATAAGTTCAGTCGACCATGTAACCGCCGGAA
─────┼─────┼─────┼─────┼─────┼─────┼─────┼─────┼─────┼─────┼─────┼─────┼─────┼── 5180
CCAGACCTCTGACGGACCCGAATGTGTGTGGTTCCGCCCTATTCAAGTCAGCTGGTACATTGGCGGCCTT

AAGATCTACTGGTCTGTGACAGCATGGGACGAACTAGAGTGGTTTGCCAAAGCAACAACAGGTTGACCGA
─────┼─────┼─────┼─────┼─────┼─────┼─────┼─────┼─────┼─────┼─────┼─────┼─────┼── 5250
TTCTAGATGACCAGACACTGTCGTACCCTGCTTGATCTCACCAAACGGTTTCGTTGTTGTCCAACTGGCT

TGAGACAGAGTATGGCGTCAAGACTGACTCAGGGTGCCCAGACGGTGCCAGATGTTATGTGTTAAATCCA
─────┼─────┼─────┼─────┼─────┼─────┼─────┼─────┼─────┼─────┼─────┼─────┼─────┼── 5320
ACTCTGTCTCATACCGCAGTTCTGACTGAGTCCCACGGGTCTGCCACGGTCTACAATACACAATTTAGGT

GAGGCCGTTAACATATCAGGATCCAAAGGGGCAGTCGTTCACCTCCAAAAGACAGGTGGAGAATTCACGT
─────┼─────┼─────┼─────┼─────┼─────┼─────┼─────┼─────┼─────┼─────┼─────┼─────┼── 5390
CTCCGGCAATTGTATAGTCCTAGGTTTCCCCGTCAGCAAGTGGAGGTTTTCTGTCCACCTCTTAAGTGCA

GTGTCACCGCATCAGGCACACCGGCTTTCTTCGACCTAAAAAACTTGAAAGGATGGTCAGGCTTGCCTAT
─────┼─────┼─────┼─────┼─────┼─────┼─────┼─────┼─────┼─────┼─────┼─────┼─────┼── 5460
CACAGTGGCGTAGTCCGTGTGGCCGAAAGAAGCTGGATTTTTTGAACTTTCCTACCAGTCCGAACGGATA

ATTTGAAGCCTCCAGCGGGAGGGTGGTTGGCAGAGTCAAAGTAGGGAAGAATGAAGAGTCTAAACCTACA
─────┼─────┼─────┼─────┼─────┼─────┼─────┼─────┼─────┼─────┼─────┼─────┼─────┼── 5530
TAAACTTCGGAGGTCGCCCTCCCACCAACCGTCTCAGTTTCATCCCTTCTTACTTCTCAGATTTGGATGT

AAAATAATGAGTGGAATCCAGACCGTCTCAAAAAACAGAGCAGACCTGACCGAGATGGTCAAGAAGATAA
─────┼─────┼─────┼─────┼─────┼─────┼─────┼─────┼─────┼─────┼─────┼─────┼─────┼── 5600
TTTTATTACTCACCTTAGGTCTGGCAGAGTTTTTTGTCTCGTCTGGACTGGCTCTACCAGTTCTTCTATT

CCAGCATGAACAGGGGAGACTTCAAGCAGATTACTTTGGCAACAGGGGCAGGCAAAACCACAGAACTCCC
─────┼─────┼─────┼─────┼─────┼─────┼─────┼─────┼─────┼─────┼─────┼─────┼─────┼── 5670
GGTCGTACTTGTCCCCTCTGAAGTTCGTCTAATGAAACCGTTGTCCCCGTCCGTTTTGGTGTCTTGAGGG
```

FIG. 21

```
AAAAGCAGTTATAGAGGAGATAGGAAGACACAAGAGAGTATTAGTTCTTATACCATTAAGGGCAGCGGCA
----+----|----+----|----+----|----+----|----+----|----+----|----+----  5740
TTTTCGTCAATATCTCCTCTATCCTTCTGTGTTCTCTCATAATCAAGAATATGGTAATTCCCGTCGCCGT

GAGTCAGTCTACCAGTATATGAGATTGAAACACCCAAGCATCTCTTTTAACCTAAGGATAGGGGACATGA
----+----|----+----|----+----|----+----|----+----|----+----|----+----  5810
CTCAGTCAGATGGTCATATACTCTAACTTTGTGGGTTCGTAGAGAAAATTGGATTCCTATCCCCTGTACT

AAGAGGGGGACATGGCAACCGGGATAACCTATGCATCATACGGGTACTTCTGCCAAATGCCTCAACCAAA
----+----|----+----|----+----|----+----|----+----|----+----|----+----  5880
TTCTCCCCCTGTACCGTTGGCCCTATTGGATACGTAGTATGCCCATGAAGACGGTTTACGGAGTTGGTTT

GCTCAGAGCTGCTATGGTAGAATACTCATACATATTCTTAGATGAATACCATTGTGCCACTCCTGAACAA
----+----|----+----|----+----|----+----|----+----|----+----|----+----  5950
CGAGTCTCGACGATACCATCTTATGAGTATGTATAAGAATCTACTTATGGTAACACGGTGAGGACTTGTT

CTGGCAATTATCGGGAAGATCCACAGATTTTCAGAGAGTATAAGGGTTGTCGCCATGACTGCCACGCCAG
----+----|----+----|----+----|----+----|----+----|----+----|----+----  6020
GACCGTTAATAGCCCTTCTAGGTGTCTAAAAGTCTCTCATATTCCCAACAGCGGTACTGACGGTGCGGTC

CAGGGTCGGTGACCACAACAGGTCAAAAGCACCCAATAGAGGAATTCATAGCCCCCGAGGTAATGAAAGG
----+----|----+----|----+----|----+----|----+----|----+----|----+----  6090
GTCCCAGCCACTGGTGTTGTCCAGTTTTCGTGGGTTATCTCCTTAAGTATCGGGGGCTCCATTACTTTCC

GGAGGATCTTGGTAGTCAGTTCCTTGATATAGCAGGGTTAAAAATACCAGTGGATGAGATGAAAGGCAAT
----+----|----+----|----+----|----+----|----+----|----+----|----+----  6160
CCTCCTAGAACCATCAGTCAAGGAACTATATCGTCCCAATTTTTATGGTCACCTACTCTACTTTCCGTTA

ATGTTGGTTTTTGTACCAACGAGAAACATGGCAGTAGAGGTAGCAAAGAAGCTAAAAGCTAAGGGCTATA
----+----|----+----|----+----|----+----|----+----|----+----|----+----  6230
TACAACCAAAAACATGGTTGCTCTTTGTACCGTCATCTCCATCGTTTCTTCGATTTTCGATTCCCGATAT

ACTCTGGATACTATTACAGTGGAGAGGATCCAGCCAATCTGAGAGTTGTGACATCACAATCCCCCTATGT
----+----|----+----|----+----|----+----|----+----|----+----|----+----  6300
TGAGACCTATGATAATGTCACCTCTCCTAGGTCGGTTAGACTCTCAACACTGTAGTGTTAGGGGGATACA
```

FIG. 2J

```
AATCGTCGCTACAAATGCTATTGAATCAGGAGTGACACTACCAGATTTGGACACGGTTATAGACACGGGG
────┼────┼────┼────┼────┼────┼────┼────┼────┼────┼────┼────┼────┼──── 6370
TTAGCACCGATGTTTACGATAACTTAGTCCTCACTGTGATGGTCTAAACCTGTGCCAATATCTGTGCCCC

TTGAAATGTGAAAAGAGGGTGAGGGTATCATCAAAGATACCCTTCATCGTAACAGGCCTTAAGAGGATGG
────┼────┼────┼────┼────┼────┼────┼────┼────┼────┼────┼────┼────┼──── 6440
AACTTTACACTTTTCTCCCACTCCCATAGTAGTTTCTATGGGAAGTAGCATTGTCCGGAATTCTCCTACC

CCGTGACTGTGGGTGAGCAGGCGCAGCGTAGGGGCAGAGTAGGTAGAGTGAAACCCGGGAGGTATTATAG
────┼────┼────┼────┼────┼────┼────┼────┼────┼────┼────┼────┼────┼──── 6510
GGCACTGACACCCACTCGTCCGCGTCGCATCCCCGTCTCATCCATCTCACTTTGGGCCCTCCATAATATC

GAGCCAGGAAACAGCAACAGGGTCAAAGGACTACCACTATGACCTCTTGCAGGCACAAAGATACGGGATT
────┼────┼────┼────┼────┼────┼────┼────┼────┼────┼────┼────┼────┼──── 6580
CTCGGTCCTTTGTCGTTGTCCCAGTTTCCTGATGGTGATACTGGAGAACGTCCGTGTTTCTATGCCCTAA

GAGGATGGAATCAACGTGACGAAATCCTTTAGGGAGATGAATTACGATTGGAGCCTATACGAGGAGGACA
────┼────┼────┼────┼────┼────┼────┼────┼────┼────┼────┼────┼────┼──── 6650
CTCCTACCTTAGTTGCACTGCTTTAGGAAATCCCTCTACTTAATGCTAACCTCGGATATGCTCCTCCTGT

GCCTACTAATAACCCAGCTGGAAATACTAAATAATCTACTCATCTCAGAAGACTTGCCAGCCGCTGTTAA
────┼────┼────┼────┼────┼────┼────┼────┼────┼────┼────┼────┼────┼──── 6720
CGGATGATTATTGGGTCGACCTTTATGATTTATTAGATGAGTAGAGTCTTCTGAACGGTCGGCGACAATT

GAACATAATGGCCAGGACTGATCACCCAGAGCCAATCCAACTTGCATACAACAGCTATGAAGTCCAGGTC
────┼────┼────┼────┼────┼────┼────┼────┼────┼────┼────┼────┼────┼──── 6790
CTTGTATTACCGGTCCTGACTAGTGGGTCTCGGTTAGGTTGAACGTATGTTGTCGATACTTCAGGTCCAG

CCGGTCCTATTCCCAAAAATAAGGAATGGAGAAGTCACAGACACCTACGAAAATTACTCGTTTCTAAATG
────┼────┼────┼────┼────┼────┼────┼────┼────┼────┼────┼────┼────┼──── 6860
GGCCAGGATAAGGGTTTTTATTCCTTACCTCTTCAGTGTCTGTGGATGCTTTTAATGAGCAAAGATTTAC

CCAGAAAGTTAGGGGAGGATGTGCCCGTGTATATCTACGCTACTGAAGATGAGGATCTGGCAGTTGACCT
────┼────┼────┼────┼────┼────┼────┼────┼────┼────┼────┼────┼────┼──── 6930
GGTCTTTCAATCCCCTCCTACACGGGCACATATAGATGCGATGACTTCTACTCCTAGACCGTCAACTGGA
```

FIG. 2K

```
CTTAGGGCTAGACTGGCCTGATCCTGGGAACCAGCAGGTAGTGGAGACTGGTAAAGCACTGAAGCAAGTG
                                                                      7000
GAATCCCGATCTGACCGGACTAGGACCCTTGGTCGTCCATCACCTCTGACCATTTCGTGACTTCGTTCAC

ACCGGGTTGTCCTCGGCTGAAAATGCCCTACTAGTGGCTTTATTTGGGTATGTGGGTTACCAGGCTCTCT
                                                                      7070
TGGCCCAACAGGAGCCGACTTTTACGGGATGATCACCGAAATAAACCCATACACCCAATGGTCCGAGAGA

CAAAGAGGCATGTCCCAATGATAACAGACATATATACCATCGAGGACCAGAGACTAGAAGACACCACCCA
                                                                      7140
GTTTCTCCGTACAGGGTTACTATTGTCTGTATATATGGTAGCTCCTGGTCTCTGATCTTCTGTGGTGGGT

CCTCCAGTATGCACCCAACGCCATAAAAACCGATGGGACAGAGACTGAACTGAAAGAACTGGCGTCGGGT
                                                                      7210
GGAGGTCATACGTGGGTTGCGGTATTTTTGGCTACCCTGTCTCTGACTTGACTTTCTTGACCGCAGCCCA

GACGTGGAAAAAATCATGGGAGCCATTTCAGATTATGCAGCTGGGGGACTGGAGTTTGTTAAATCCCAAG
                                                                      7280
CTGCACCTTTTTTAGTACCCTCGGTAAAGTCTAATACGTCGACCCCCTGACCTCAAACAATTTAGGGTTC

CAGAAAAGATAAAAACAGCTCCTTTGTTTAAAGAAAACGCAGAAGCCGCAAAAGGGTATGTCCAAAAATT
                                                                      7350
GTCTTTTCTATTTTTGTCGAGGAAACAAATTTCTTTTGCGTCTTCGGCGTTTTCCCATACAGGTTTTTAA

CATTGACTCATTAATTGAAAATAAAGAAGAAATAATCAGATATGGTTTGTGGGGAACACACACAGCACTA
                                                                      7420
GTAACTGAGTAATTAACTTTTATTTCTTCTTTATTAGTCTATACCAAACACCCCTTGTGTGTGTCGTGAT

TACAAAAGCATAGCTGCAAGACTGGGGCATGAAACAGCGTTTGCCACACTAGTGTTAAAGTGGCTAGCTT
                                                                      7490
ATGTTTTCGTATCGACGTTCTGACCCCGTACTTTGTCGCAAACGGTGTGATCACAATTTCACCGATCGAA

TTGGAGGGGAATCAGTGTCAGACCACGTCAAGCAGGCGGCAGTTGATTTAGTGGTCTATTATGTGATGAA
                                                                      7560
AACCTCCCCTTAGTCACAGTCTGGTGCAGTTCGTCCGCCGTCAACTAAATCACCAGATAATACACTACTT
```

FIG. 2L

```
TAAGCCTTCCTTCCCAGGTGACTCCGAGACACAGCAAGAAGGGAGGCGATTCGTCGCAAGCCTGTTCATC
                                                                      7630
ATTCGGAAGGAAGGGTCCACTGAGGCTCTGTGTCGTTCTTCCCTCCGCTAAGCAGCGTTCGGACAAGTAG

TCCGCACTGGCAACCTACACATACAAAACTTGGAATTACCACAATCTCTCTAAAGTGGTGGAACCAGCCC
                                                                      7700
AGGCGTGACCGTTGGATGTGTATGTTTTGAACCTTAATGGTGTTAGAGAGATTTCACCACCTTGGTCGGG

TGGCTTACCTCCCCTATGCTACCAGCGCATTAAAAATGTTCACCCCAACGCGGCTGGAGAGCGTGGTGAT
                                                                      7770
ACCGAATGGAGGGGATACGATGGTCGCGTAATTTTTACAAGTGGGGTTGCGCCGACCTCTCGCACCACTA

ACTGAGCACCACGATATATAAAACATACCTCTCTATAAGGAAGGGGAAGAGTGATGGATTGCTGGGTACG
                                                                      7840
TGACTCGTGGTGCTATATATTTTGTATGGAGAGATATTCCTTCCCCTTCTCACTACCTAACGACCCATGC

GGGATAAGTGCAGCCATGGAAATCCTGTCACAAAACCCAGTATCGGTAGGTATATCTGTGATGTTGGGGG
                                                                      7910
CCCTATTCACGTCGGTACCTTTAGGACAGTGTTTTGGGTCATAGCCATCCATATAGACACTACAACCCCC

TAGGGGCAATCGCTGCGCACAACGCTATTGAGTCCAGTGAACAGAAAAGGACCCTACTTATGAAGGTGTT
                                                                      7980
ATCCCCGTTAGCGACGCGTGTTGCGATAACTCAGGTCACTTGTCTTTTCCTGGGATGAATACTTCCACAA

TGTAAAGAACTTCTTGGATCAGGCTGCAACAGATGAGCTGGTAAAAGAAAACCCAGAAAAAATTATAATG
                                                                      8050
ACATTTCTTGAAGAACCTAGTCCGACGTTGTCTACTCGACCATTTTCTTTTGGGTCTTTTTTAATATTAC

GCCTTATTTGAAGCAGTCCAGACAATTGGTAACCCCCTGAGACTAATATACCACCTGTATGGGGTTTACT
                                                                      8120
CGGAATAAACTTCGTCAGGTCTGTTAACCATTGGGGGACTCTGATTATATGGTGGACATACCCCAAATGA

ACAAAGGTTGGGAGGCCAAGGAACTATCTGAGAGGACAGCAGGCAGAAACTTATTCACATTGATAATGTT
                                                                      8190
TGTTTCCAACCCTCCGGTTCCTTGATAGACTCTCCTGTCGTCCGTCTTTGAATAAGTGTAACTATTACAA
```

FIG. 2M

```
TGAAGCCTTCGAGTTATTAGGGATGGACTCACAAGGGAAAATAAGGAACCTGTCCGGAAATTACATTTTG
───┼───┼───┼───┼───┼───┼───┼───┼───┼───┼───┼───┼───┼───┼ 8260
ACTTCGGAAGCTCAATAATCCCTACCTGAGTGTTCCCTTTTATTCCTTGGACAGGCCTTTAATGTAAAAC

GATTTGATATACGGCCTACACAAGCAAATCAACAGAGGGCTGAAGAAAATGGTACTGGCGTGGGCCCTG
───┼───┼───┼───┼───┼───┼───┼───┼───┼───┼───┼───┼───┼───┼ 8330
CTAAACTATATGCCGGATGTGTTCGTTTAGTTGTCTCCCGACTTCTTTTACCATGACCCCACCCGGGCAC

CACCCTTTAGTTGTGACTGGACCCCTAGTGACGAGAGGATCAGATTGCCAACAGACAACTATTTGAGGGT
───┼───┼───┼───┼───┼───┼───┼───┼───┼───┼───┼───┼───┼───┼ 8400
GTGGGAAATCAACACTGACCTGGGGATCACTGCTCTCCTAGTCTAACGGTTGTCTGTTGATAAACTCCCA

AGAAACCAGGTGCCCATGTGGCTATGAGATGAAAGCTTTCAAAAATGTAGGTGGCAAACTTACCAAAGTG
───┼───┼───┼───┼───┼───┼───┼───┼───┼───┼───┼───┼───┼───┼ 8470
TCTTTGGTCCACGGGTACACCGATACTCTACTTTCGAAAGTTTTTACATCCACCGTTTGAATGGTTTCAC

GAGGAGAGCGGGCCTTTCCTATGTAGAAACAGACCTGGTAGGGGACCAGTCAACTACAGAGTCACCAAGT
───┼───┼───┼───┼───┼───┼───┼───┼───┼───┼───┼───┼───┼───┼ 8540
CTCCTCTCGCCCGGAAAGGATACATCTTTGTCTGGACCATCCCCTGGTCAGTTGATGTCTCAGTGGTTCA

ATTACGATGACAACCTCAGAGAGATAAAACCAGTAGCAAAGTTGGAAGGACAGGTAGAGCACTACTACAA
───┼───┼───┼───┼───┼───┼───┼───┼───┼───┼───┼───┼───┼───┼ 8610
TAATGCTACTGTTGGAGTCTCTCTATTTTGGTCATCGTTTCAACCTTCCTGTCCATCTCGTGATGATGTT

AGGGGTCACAGCAAAAATTGACTACAGTAAAGGAAAAATGCTCTTGGCCACTGACAAGTGGGAGGTGGAA
───┼───┼───┼───┼───┼───┼───┼───┼───┼───┼───┼───┼───┼───┼ 8680
TCCCCAGTGTCGTTTTTAACTGATGTCATTTCCTTTTTACGAGAACCGGTGACTGTTCACCCTCCACCTT

CATGGTGTCATAACCAGGTTAGCTAAGAGATATACTGGGGTCGGGTTCAATGGTGCATACTTAGGTGACG
───┼───┼───┼───┼───┼───┼───┼───┼───┼───┼───┼───┼───┼───┼ 8750
GTACCACAGTATTGGTCCAATCGATTCTCTATATGACCCCAGCCCAAGTTACCACGTATGAATCCACTGC

AGCCCAATCACCGTGCTCTAGTGGAGAGGGACTGTGCAACTATAACCAAAAACACAGTACAGTTTCTAAA
───┼───┼───┼───┼───┼───┼───┼───┼───┼───┼───┼───┼───┼───┼ 8820
TCGGGTTAGTGGCACGAGATCACCTCTCCCTGACACGTTGATATTGGTTTTTGTGTCATGTCAAAGATTT
```

FIG. 2N

```
AATGAAGAAGGGGTGTGCGTTCACCTATGACCTGACCATCTCCAATCTGACCAGGCTCATCGAACTAGTA
----+----+----+----+----+----+----+----+----+----+----+----+----+ 8890
TTACTTCTTCCCCACACGCAAGTGGATACTGGACTGGTAGAGGTTAGACTGGTCCGAGTAGCTTGATCAT

CACAGGAACAATCTTGAAGAGAAGGAAATACCCACCGCTACGGTCACCACATGGCTAGCTTACACCTTCG
----+----+----+----+----+----+----+----+----+----+----+----+----+ 8960
GTGTCCTTGTTAGAACTTCTCTTCCTTTATGGGTGGCGATGCCAGTGGTGTACCGATCGAATGTGGAAGC

TGAATGAAGACGTAGGGACTATAAAACCAGTACTAGGAGAGAGAGTAATCCCCGACCCTGTAGTTGATAT
----+----+----+----+----+----+----+----+----+----+----+----+----+ 9030
ACTTACTTCTGCATCCCTGATATTTTGGTCATGATCCTCTCTCTCATTAGGGGCTGGGACATCAACTATA

CAATTTACAACCAGAGGTGCAAGTGGACACGTCAGAGGTTGGGATCACAATAATTGGAAGGGAAACCCTG
----+----+----+----+----+----+----+----+----+----+----+----+----+ 9100
GTTAAATGTTGGTCTCCACGTTCACCTGTGCAGTCTCCAACCCTAGTGTTATTAACCTTCCCTTTGGGAC

ATGACAACGGGAGTGACACCTGTCTTGGAAAAAGTAGAGCCTGACGCCAGCGACAACCAAAACTCGGTGA
----+----+----+----+----+----+----+----+----+----+----+----+----+ 9170
TACTGTTGCCCTCACTGTGGACAGAACCTTTTTCATCTCGGACTGCGGTCGCTGTTGGTTTTGAGCCACT

AGATCGGGTTGGATGAGGGTAATTACCCAGGGCCTGGAATACAGACACATACACTAACAGAAGAAATACA
----+----+----+----+----+----+----+----+----+----+----+----+----+ 9240
TCTAGCCCAACCTACTCCCATTAATGGGTCCCGGACCTTATGTCTGTGTATGTGATTGTCTTCTTTATGT

CAACAGGGATGCGAGGCCCTTCATCATGATCCTGGGCTCAAGGAATTCCATATCAAATAGGGCAAAGACT
----+----+----+----+----+----+----+----+----+----+----+----+----+ 9310
GTTGTCCCTACGCTCCGGGAAGTAGTACTAGGACCCGAGTTCCTTAAGGTATAGTTTATCCCGTTTCTGA

GCTAGAAATATAAATCTGTACACAGGAAATGACCCCAGGGAAATACGAGACTTGATGGCTGCAGGGCGCA
----+----+----+----+----+----+----+----+----+----+----+----+----+ 9380
CGATCTTTATATTTAGACATGTGTCCTTTACTGGGGTCCCTTTATGCTCTGAACTACCGACGTCCCGCGT

TGTTAGTAGTAGCACTGAGGGATGTCGACCCTGAGCTGTCTGAAATGGTCGATTTCAAGGGGACTTTTTT
----+----+----+----+----+----+----+----+----+----+----+----+----+ 9450
ACAATCATCATCGTGACTCCCTACAGCTGGGACTCGACAGACTTTACCAGCTAAAGTTCCCCTGAAAAAA
```

FIG. 20

```
AGATAGGGAGGCCCTGGAGGCTCTAAGTCTCGGGCAACCTAAACCGAAGCAGGTTACCAACGAAGCTGTT
                                                                        9520
TCTATCCCTCCGGACCTCCGAGATTCAGAGCCCGTTGGATTTGGCTTCGTCCAATGGTTCCTTCGACAA

AGGAATTTGATAGAACAGAAAAAAGATGTGGAGATCCCTAACTGGTTTGCATCAGATGACCCAGTATTTC
                                                                        9590
TCCTTAAACTATCTTGTCTTTTTTCTACACCTCTAGGGATTGACCAAACGTAGTCTACTGGGTCATAAAG

TGGAAGTGGCCTTAAAAAATGATAAGTACTACTTAGTAGGAGATGTTGGAGAGCTAAAAGATCAAGCTAA
                                                                        9660
ACCTTCACCGGAATTTTTTACTATTCATGATGAATCATCCTCTACAACCTCTCGATTTTCTAGTTCGATT

AGCACTTGGGGCCACGGATCAGACAAGAATTATAAAGGAGGTAGGCTCAAGGACGTATGCCATGAAGCTA
                                                                        9730
TCGTGAACCCCGGTGCCTAGTCTGTTCTTAATATTTCCTCCATCCGAGTTCCTGCATACGGTACTTCGAT

TCTAGCTGGTTCCTCAAGGCATCAAACAAACAGATGAGTTTAACTCCACTGTTTGAGGAATTGTTGCTAC
                                                                        9800
AGATCGACCAAGGAGTTCCGTAGTTTGTTTGTCTACTCAAATTGAGGTGACAAACTCCTTAACAACGATG

GGTGCCCACCTGCAACTAAGAGCAATAAGGGGCACATGGCATCAGCTTACCAATTGGCACAGGGTAACTG
                                                                        9870
CCACGGGTGGACGTTGATTCTCGTTATTCCCCGTGTACCGTAGTCGAATGGTTAACCGTGTCCCATTGAC

GGAGCCCCTCGGTTGCGGGGTGCACCTAGGTACAATACCAGCCAGAAGGGTGAAGATACACCCATATGAA
                                                                        9940
CCTCGGGGAGCCAACGCCCCACGTGGATCCATGTTATGGTCGGTCTTCCCACTTCTATGTGGGTATACTT

GCTTACCTGAAGTTGAAAGATTTCATAGAAGAAGAAGAGAAGAAACCTAGGGTTAAGGATACAGTAATAA
                                                                        10010
CGAATGGACTTCAACTTTCTAAAGTATCTTCTTCTTCTCTTCTTTGGATCCCAATTCCTATGTCATTATT

GAGAGCACAACAAATGGATACTTAAAAAAATAAGGTTTCAAGGAAACCTCAACACCAAGAAAATGCTCAA
                                                                        10080
CTCTCGTGTTGTTTACCTATGAATTTTTTTATTCCAAAGTTCCTTTGGAGTTGTGGTTCTTTTACGAGTT
```

FIG. 2P

```
CCCAGGGAAACTATCTGAACAGTTGGACAGGGAGGGGCGCAAGAGGAACATCTACAACCACCAGATTGGT
                                                                      + 10150
GGGTCCCTTTGATAGACTTGTCAACCTGTCCCTCCCCGCGTTCTCCTTGTAGATGTTGGTGGTCTAACCA

ACTATAATGTCAAGTGCAGGCATAAGGCTGGAGAAATTGCCAATAGTGAGGGCCCAAACCGACACCAAAA
                                                                      + 10220
TGATATTACAGTTCACGTCCGTATTCCGACCTCTTTAACGGTTATCACTCCCGGGTTTGGCTGTGGTTTT

CCTTTCATGAGGCAATAAGAGATAAGATAGACAAGAGTGAAAACCGGCAAAATCCAGAATTGCACAACAA
                                                                      + 10290
GGAAAGTACTCCGTTATTCTCTATTCTATCTGTTCTCACTTTTGGCCGTTTTACGTCTTAACGTGTTGTT

ATTGTTGGAGATTTTCCACACGATAGCCCAACCCACCCTGAAACACACCTACGGTGAGGTGACGTGGGAG
                                                                      + 10360
TAACAACCTCTAAAAGGTGTGCTATCGGGTTGGGTGGGACTTTGTGTGGATGCCACTCCACTGCACCCTC

CAACTTGAGGCGGGGGTAAATAGAAAGGGGGCAGCAGGCTTCCTGGAGAAGAAGAACATCGGAGAAGTAT
                                                                      + 10430
GTTGAACTCCGCCCCATTTATCTTTCCCCCGTCGTCCGAAGGACCTCTTCTTCTTGTAGCCTCTTCATA

TGGATTCAGAAAAGCACCTGGTAGAACAATTGGTCAGGGATCTGAACGCCGGGAGAAAGATAAAATATTA
                                                                      + 10500
ACCTAAGTCTTTTCGTGGACCATCTTGTTAACCAGTCCCTAGACTTCCGGCCCTCTTTCTATTTTATAAT

TGAAACTGCAATACCAAAAAATGAGAAGAGAGATGTCAGTGATGACTGGCAGGCAGGGGACCTGGTGGTT
                                                                      + 10570
ACTTTGACGTTATGGTTTTTTACTCTTCTCTCTACAGTCACTACTGACCGTCCGTCCCCTGGACCACCAA

GAGAAGAGGCCAAGAGTTATCCAATACCCTGAAGCCAAGACAAGGCTAGCCATCACTAAGGTCATGTATA
                                                                      + 10640
CTCTTCTCCGGTTCTCAATAGGTTATGGGACTTCGGTTCTGTTCCGATCGGTAGTGATTCCAGTACATAT

ACTGGGTGAAACAGCAGCCCGTTGTGATTCCAGGATATGAAGGAAAGACCCCCTTGTTCAACATCTTTGA
                                                                      + 10710
TGACCCACTTTGTCGTCGGGCAACACTAAGGTCCTATACTTCCTTTCTGGGGGAACAAGTTGTAGAAACT
```

FIG. 2Q

```
TAAAGTGAGAAAGGAATGGGACTCGTTCAATGAGCCAGTGGCCGTAAGTTTTGACACCAAAGCCTGGGAC
----+----+----+----+----+----+----+----+----+----+----+----+----+----+ 10780
ATTTCACTCTTTCCTTACCCTGAGCAAGTTACTCGGTCACCGGCATTCAAAACTGTGGTTTCGGACCCTG

ACTCAAGTGACTAGTAAGGATCTGCAACTTATTGGAGAAATCCAGAAATATTACTATAAGAAGGAGTGGC
----+----+----+----+----+----+----+----+----+----+----+----+----+----+ 10850
TGAGTTCACTGATCATTCCTAGACGTTGAATAACCTCTTTAGGTCTTTATAATGATATTCTTCCTCACCG

ACAAGTTCATTGACACCATCACCGACCACATGACAGAAGTACCAGTTATAACAGCAGATGGTGAAGTATA
----+----+----+----+----+----+----+----+----+----+----+----+----+----+ 10920
TGTTCAAGTAACTGTGGTAGTGGCTGGTGTACTGTCTTCATGGTCAATATTGTCGTCTACCACTTCATAT

TATAAGAAATGGGCAGAGAGGGAGCGGCCAGCCAGACACAAGTGCTGGCAACAGCATGTTAAATGTCCTG
----+----+----+----+----+----+----+----+----+----+----+----+----+----+ 10990
ATATTCTTTACCCGTCTCTCCCTCGCCGGTCGGTCTGTGTTCACGACCGTTGTCGTACAATTTACAGGAC

ACAATGATGTACGGCTTCTGCGAAAGCACAGGGGTACCGTACAAGAGTTTCAACAGGGTGGCAAGGATCC
----+----+----+----+----+----+----+----+----+----+----+----+----+----+ 11060
TGTTACTACATGCCGAAGACGCTTTCGTGTCCCCATGGCATGTTCTCAAAGTTGTCCCACCGTTCCTAGG

ACGTCTGTGGGATGATGGCTTCTTAATAACTGAAAAAGGGTTAGGGCTGAAATTTGCTAACAAAGGGAT
----+----+----+----+----+----+----+----+----+----+----+----+----+----+ 11130
TGCAGACACCCCTACTACCGAAGAATTATTGACTTTTTCCCAATCCCGACTTTAAACGATTGTTTCCCTA

GCAGATTCTTCATGAAGCAGGCAAACCTCAGAAGATAACGGAAGGGGAAAAGATGAAAGTTGCCTATAGA
----+----+----+----+----+----+----+----+----+----+----+----+----+----+ 11200
CGTCTAAGAAGTACTTCGTCCGTTTGGAGTCTTCTATTGCCTTCCCCTTTTCTACTTTCAACGGATATCT

TTTGAGGATATAGAGTTCTGTTCTCATACCCCAGTCCCTGTTAGGTGGTCCGACAACACCAGTAGTCACA
----+----+----+----+----+----+----+----+----+----+----+----+----+----+ 11270
AAACTCCTATATCTCAAGACAAGAGTATGGGGTCAGGGACAATCCACCAGGCTGTTGTGGTCATCAGTGT

TGGCCGGGAGAGACACCGCTGTGATACTATCAAAGATGGCAACAAGATTGGATTCAAGTGGAGAGAGGGG
----+----+----+----+----+----+----+----+----+----+----+----+----+----+ 11340
ACCGGCCCTCTCTGTGGCGACACTATGATAGTTTCTACCGTTGTTCTAACCTAAGTTCACCTCTCTCCCC
```

FIG. 2R

```
TACCACAGCATATGAAAAAGCGGTAGCCTTCAGTTTCTTGCTGATGTATTCCTGGAACCCGCTTGTTAGG
——————+——————+——————+——————+——————+——————+——————+——————+——————+——————+——————+——————+——————+—— 11410
ATGGTGTCGTATACTTTTTCGCCATCGGAAGTCAAAGAACGACTACATAAGGACCTTGGGCGAACAATCC

AGGATTTGCCTGTTGGTCCTTTCGCAACAGCCAGAGACAGACCCATCAAAACATGCCACTTATTATTACA
——————+——————+——————+——————+——————+——————+——————+——————+——————+——————+——————+——————+——————+—— 11480
TCCTAAACGGACAACCAGGAAAGCGTTGTCGGTCTCTGTCTGGGTAGTTTTGTACGGTGAATAATAATGT

AAGGTGATCCAATAGGGGCCTATAAAGATGTAATAGGTCGGAATCTAAGTGAACTGAAGAGAACAGGCTT
——————+——————+——————+——————+——————+——————+——————+——————+——————+——————+——————+——————+——————+—— 11550
TTCCACTAGGTTATCCCCGGATATTTCTACATTATCCAGCCTTAGATTCACTTGACTTCTCTTGTCCGAA

TGAGAAATTGGCAAATCTAAACCTAAGCCTGTCCACGTTGGGGGTCTGGACTAAGCACACAAGCAAAAGA
——————+——————+——————+——————+——————+——————+——————+——————+——————+——————+——————+——————+——————+—— 11620
ACTCTTTAACCGTTTAGATTTGGATTCGGACAGGTGCAACCCCAGACCTGATTCGTGTGTTCGTTTTCT

ATAATTCAGGACTGTGTTGCCATTGGGAAAGAAGAGGGCAACTGGCTAGTTAAGCCCGACAGGCTGATAT
——————+——————+——————+——————+——————+——————+——————+——————+——————+——————+——————+——————+——————+—— 11690
TATTAAGTCCTGACACAACGGTAACCCTTTCTTCTCCCGTTGACCGATCAATTCGGGCTGTCCGACTATA

CCAGCAAAACTGGCCACTTATACATACCTGATAAAGGCTTTACATTACAAGGAAAGCATTATGAGCAACT
——————+——————+——————+——————+——————+——————+——————+——————+——————+——————+——————+——————+——————+—— 11760
GGTCGTTTTGACCGGTGAATATGTATGGACTATTTCCGAAATGTAATGTTCCTTTCGTAATACTCGTTGA

GCAGCTAAGAACAGAGACAAACCCGGTCATGGGGGTTGGGACTGAGAGATACAAGTTAGGTCCCATAGTC
——————+——————+——————+——————+——————+——————+——————+——————+——————+——————+——————+——————+——————+—— 11830
CGTCGATTCTTGTCTCTGTTTGGGCCAGTACCCCCAACCCTGACTCTCTATGTTCAATCCAGGGTATCAG

AATCTGCTGCTGAGAAGGTTGAAAATTCTGCTCATGACGGCCGTCGGCGTCAGCAGCTGAGACAAAATGT
——————+——————+——————+——————+——————+——————+——————+——————+——————+——————+——————+——————+——————+—— 11900
TTAGACGACGACTCTTCCAACTTTTAAGACGAGTACTGCCGGCAGCCGCAGTCGTCGACTCTGTTTTACA

ATATATTGTAAATAAATTAATCCATGTACATAGTGTATATAAATATAGTTGGGACCGTCCACCTCAAGAA
——————+——————+——————+——————+——————+——————+——————+——————+——————+——————+——————+——————+——————+—— 11970
TATATAACATTTATTTAATTAGGTACATGTATCACATATATTTATATCAACCCTGGCAGGTGGAGTTCTT
```

FIG. 2S

```
GACGACACGCCCAACACGCACAGCTAAACAGTAGTCAAGATTATCTACCTCAAGATAACACTACATTTAA
————+————+————+————+————+————+————+————+————+————+————+————+————+ 12040
CTGCTGTGCGGGTTGTGCGTGTCGATTTGTCATCAGTTCTAATAGATGGAGTTCTATTGTGATGTAAATT

TGCACACAGCACTTTAGCTGTATGAGGATACGCCCGACGTCTATAGTTGGACTAGGGAAGACCTCTAACA
————+————+————+————+————+————+————+————+————+————+————+————+————+ 12110
ACGTGTGTCGTGAAATCGACATACTCCTATGCGGGCTGCAGATATCAACCTGATCCCTTCTGGAGATTGT

GCCCCGCGGATCTAGAGGAGCATGCGACGTCAGGTGGCACTTTTCGGGGAAATGTGCGCGGAACCCCTA
————+————+————+————+————+————+————+————+————+————+————+————+————+ 12180
CGGGGCGCCTAGATCTCCTCGTACGCTGCAGTCCACCGTGAAAAGCCCCTTTACACGCGCCTTGGGGAT

TTTGTTTATTTTTCTAAATACATTCAAATATGTATCCGCTCATGAGACAATAACCCTGATAAATGCTTCA
————+————+————+————+————+————+————+————+————+————+————+————+————+ 12250
AAACAAATAAAAAGATTTATGTAAGTTTATACATAGGCGAGTACTCTGTTATTGGGACTATTTACGAAGT

ATAATATTGAAAAAGGAAGAGTATGAGTATTCAACATTTCCGTGTCGCCCTTATTCCCTTTTTTGCGGCA
————+————+————+————+————+————+————+————+————+————+————+————+————+ 12320
TATTATAACTTTTTCCTTCTCATACTCATAAGTTGTAAAGGCACAGCGGGAATAAGGGAAAAAACGCCGT

TTTTGCCTTCCTGTTTTTGCTCACCCAGAAACGCTGGTGAAAGTAAAAGATGCTGAAGATCAGTTGGGTG
————+————+————+————+————+————+————+————+————+————+————+————+————+ 12390
AAAACGGAAGGACAAAAACGAGTGGGTCTTTGCGACCACTTTCATTTTCTACGACTTCTAGTCAACCCAC

CACGAGTGGGTTACATCGAACTGGATCTCAACAGCGGTAAGATCCTTGAGAGTTTTCGCCCCGAAGAACG
————+————+————+————+————+————+————+————+————+————+————+————+————+ 12460
GTGCTCACCCAATGTAGCTTGACCTAGAGTTGTCGCCATTCTAGGAACTCTCAAAAGCGGGGCTTCTTGC

TTTTCCAATGATGAGCACTTTTAAAGTTCTGCTATGTGGCGCGGTATTATCCCGTATTGACGCCGGGCAA
————+————+————+————+————+————+————+————+————+————+————+————+————+ 12530
AAAAGGTTACTACTCGTGAAAATTTCAAGACGATACACCGCGCCATAATAGGGCATAACTGCGGCCCGTT

GAGCAACTCGGTCGCCGCATACACTATTCTCAGAATGACTTGGTTGAGTACTCACCAGTCACAGAAAAGC
————+————+————+————+————+————+————+————+————+————+————+————+————+ 12600
CTCGTTGAGCCAGCGGCGTATGTGATAAGAGTCTTACTGAACCAACTCATGAGTGGTCAGTGTCTTTTCG
```

FIG. 2T

```
ATCTTACGGATGGCATGACACTAAGAGAATTATGCAGTGCTGCCATAACCATGAGTGATAACACTGCGGC
--------+---------+---------+---------+---------+---------+---------+  12670
TAGAATGCCTACCGTACTGTCATTCTCTTAATACGTCACGACGGTATTGGTACTCACTATTGTGACGCCG

CAACTTACTTCTGACAACGATCGGAGGACCGAAGGAGCTAACCGCTTTTTTGCACAACATGGGGGATCAT
--------+---------+---------+---------+---------+---------+---------+  12740
GTTGAATGAAGACTGTTGCTAGCCTCCTGGCTTCCTCGATTGGCGAAAAAACGTGTTGTACCCCCTAGTA

GTAACTCGCCTTGATCGTTGGGAACCGGAGCTGAATGAAGCCATACCAAACGACGAGCGTGACACCACGA
--------+---------+---------+---------+---------+---------+---------+  12810
CATTGAGCGGAACTAGCAACCCTTGGCCTCGACTTACTTCGGTATGGTTTGCTGCTCGCACTGTGGTGCT

TGCCTGTAGCAATGGCAACAACGTTGCGCAAACTATTAACTGGCGAACTACTTACTCTAGCTTCCCGGCA
--------+---------+---------+---------+---------+---------+---------+  12880
ACGGACATCGTTACCGTTGTTGCAACGCGTTTGATAATTGACCGCTTGATGAATGAGATCGAAGGGCCGT

ACAATTAATAGACTGGATGGAGGCGGATAAAGTTGCAGGACCACTTCTGCGCTCGGCCCTTCCGGCTGGC
--------+---------+---------+---------+---------+---------+---------+  12950
TGTTAATTATCTGACCTACCTCCGCCTATTTCAACGTCCTGGTGAAGACGCGAGCCGGGAAGGCCGACCG

TGGTTTATTGCTGATAAATCTGGAGCCGGTGAGCGTGGGTCTCGCGGTATCATTGCAGCACTGGGGCCAG
--------+---------+---------+---------+---------+---------+---------+  13020
ACCAAATAACGACTATTTAGACCTCGGCCACTCGCACCCAGAGCGCCATAGTAACGTCGTGACCCCGGTC

ATGGTAAGCCCTCCCGTATCGTAGTTATCTACACGACGGGGAGTCAGGCAACTATGGATGAACGAAATAG
--------+---------+---------+---------+---------+---------+---------+  13090
TACCATTCGGGAGGGCATAGCATCAATAGATGTGCTGCCCCTCAGTCCGTTGATACCTACTTGCTTTATC

ACAGATCGCTGAGATAGGTGCCTCACTGATTAAGCATTGGTAACTGTCAGACCAAGTTTACTCATATATA
--------+---------+---------+---------+---------+---------+---------+  13160
TGTCTAGCGACTCTATCCACGGAGTGACTAATTCGTAACCATTGACAGTCTGGTTCAAATGAGTATATAT

CTTTAGATTGATTTAAAACTTCATTTTTAATTTAAAAGGATCTAGGTGAAGATCCTTTTTGATAATCTCA
--------+---------+---------+---------+---------+---------+---------+  13230
GAAATCTAACTAAATTTTGAAGTAAAAATTAAATTTTCCTAGATCCACTTCTAGGAAAAACTATTAGAGT
```

FIG. 2U

```
TGACCAAAATCCCTTAACGTGAGTTTTCGTTCCACTGAGCGTCAGACCCCGTAGAAAAGATCAAAGGATC
ACTGGTTTTAGGGAATTGCACTCAAAAGCAAGGTGACTCGCAGTCTGGGGCATCTTTTCTAGTTTCCTAG  13300

TTCTTGAGATCCTTTTTTTCTGCGCGTAATCTGCTGCTTGCAAACAAAAAAACCACCGCTACCAGCGGTG
AAGAACTCTAGGAAAAAAAGACGCGCATTAGACGACGAACGTTTGTTTTTTGGTGGCGATGGTCGCCAC  13370

GTTTGTTTGCCGGATCAAGAGCTACCAACTCTTTTTCCGAAGGTAACTGGCTTCAGCAGAGCGCAGATAC
CAAACAAACGGCCTAGTTCTCGATGGTTGAGAAAAAGGCTTCCATTGACCGAAGTCGTCTCGCGTCTATG  13440

CAAATACTGTCCTTCTAGTGTAGCCGTAGTTAGGCCACCACTTCAAGAACTCTGTAGCACCGCCTACATA
GTTTATGACAGGAAGATCACATCGGCATCAATCCGGTGGTGAAGTTCTTGAGACATCGTGGCGGATGTAT  13510

CCTCGCTCTGCTAATCCTGTTACCAGTGGCTGCTGCCAGTGGCGATAAGTCGTGTCTTACCGGGTTGGAC
GGAGCGAGACGATTAGGACAATGGTCACCGACGACGGTCACCGCTATTCAGCACAGAATGGCCCAACCTG  13580

TCAAGACGATAGTTACCGGATAAGGCGCAGCGGTCGGGCTGAACGGGGGGTTCGTGCACACAGCCCAGCT
AGTTCTGCTATCAATGGCCTATTCCGCGTCGCCAGCCCGACTTGCCCCCCAAGCACGTGTGTCGGGTCGA  13650

TGGAGCGAACGACCTACACCGAACTGAGATACCTACAGCGTGAGCTATGAGAAAGCGCCACGCTTCCCGA
ACCTCGCTTGCTGGATGTGGCTTGACTCTATGGATGTCGCACTCGATACTCTTTCGCGGTGCGAAGGGCT  13720

AGGGAGAAAGGCGGACAGGTATCCGGTAAGCGGCAGGGTCGGAACAGGAGAGCGCACGAGGGAGCTTCCA
TCCCTCTTTCCGCCTGTCCATAGGCCATTCGCCGTCCCAGCCTTGTCCTCTCGCGTGCTCCCTCGAAGGT  13790

GGGGCAAACGCCTGGTATCTTTATAGTCCTGTCGGGTTTCGCCACCTCTGACTTGAGCGTCGATTTTTGT
CCCCCTTTGCGGACCATAGAAATATCAGGACAGCCCAAAGCGGTGGAGACTGAACTCGCAGCTAAAAACA  13860
```

FIG. 2V

```
GATGCTCGTCAGGGGGGCGGAGCCTATGGAAAAACGCCAGCAACGCGGCCTTTTTACGGTTCCTGGCCTT
————+————+————+————+————+————+————+————+————+————+————+————+————+    13930
CTACGAGCAGTCCCCCCGCCTCGGATACCTTTTTGCGGTCGTTGCGCCGGAAAAATGCCAAGGACCGGAA

TTGCTGGCCTTTTGCTCACATGTTCTTTCCTGCGTTATCCCCTGATTCTGTGGATAACCGTATTACCGCC
————+————+————+————+————+————+————+————+————+————+————+————+————+    14000
AACGACCGGAAAACGAGTGTACAAGAAAGGACGCAATAGGGGACTAAGACACCTATTGGCATAATGGCGG

TTTGAGTGAGCTGATACCGCTCGCCGCAGCCGAACGACCGAGCGCAGCGAGTCAGTGAGCGAGGAAGCGG
————+————+————+————+————+————+————+————+————+————+————+————+————+    14070
AAACTCACTCGACTATGGCGAGCGGCGTCGGCTTGCTGGCTCGCGTCGCTCAGTCACTCGCTCCTTCGCC

AAGAGCGC
————+——→  14078
TTCTCGCG
```

FIG. 2W

SEQUENCE LISTING

<160> NUMBER OF SEQ ID NOS: 9

<210> SEQ ID NO 1
<211> LENGTH: 14078
<212> TYPE: DNA
<213> ORGANISM: Bovine Viral Diarrhea Virus

<400> SEQUENCE: 1

```
cacgcgtatc gatgaattcg ttaatacgac tcactatagt atacgagaat tagaaaaggc      60
actcgtatac gtattgggca attaaaaata ataattaggc ctagggaaca aatccctctc     120
agcgaaggcc gaaagaggc tagccatgcc cttagtagga ctagcataat gagggggta      180 gcaacagtgg tgagttcgtt ggatggctta agccctgagt acagggtagt cgtcagtggt      240
tcgacgcctt ggaataaagg tctcgagatg ccacgtggac gagggcatgc ccaaagcaca      300
tcttaacctg agcgggggtc gcccaggtaa aagcagtttt aaccgactgt tacgaataca      360
```

```
gcctgatagg gtgctgcaga ggcccactgt attgctacta aaatctctg ctgtacatgg      420
cacatgtcag acacgaaaga agagggagca acaaaaaaga aaacacagaa acccgacaga     480
ctagaaaggg ggaaaatgaa aatagtgccc aaagaatctg aaaaagacag caaaactaaa    540
cctccggatg ctacaatagt ggtggaagga gtcaaatacc aggtgaggaa gaagggaaaa    600
accaagagta aaacactcca ggacggcttg taccataaca aaaacaaacc tcaggaatca    660
cgcaagaaac tggaaaaagc attgttggcg tgggcaataa tagctatagt tttgtttcaa    720
gttacaatgg gagaaaacat aacacagtgg aacctacaag ataatgggac ggaagggata    780
caacgggcaa tgttccaaag gggtgtgaat agaagtttac atggaatctg ccagagaaa     840
atctgtactg gcgtcccttc ccatctagcc accgatatag aactaaaaac aattcatggt    900
atgatggatg caagtgagaa gaccaactac acgtgttgca gacttcaacg ccatgagtgg    960
aacaagcatg gttggtgcaa ctggtacaat attgaaccct ggattctagt catgaataga   1020
acccaagcca atctcactga gggacaacca ccaagggagt gcgcagtcac ttgtaggtat   1080
gatagggcta gtgacttaaa cgtggtaaca caagctagag atagccccac acccttaaca   1140
ggttgcaaga aaggaaagaa cttctccttt gcaggcatat tgatgcgggg ccctgcaac   1200
tttgaaatag ctgcaagtga tgtattattc aaagaacatg aacgcattag tatgttccag   1260
gataccactc tttaccttgt tgacggggttg accaactcct tagaaggtgc cagacaagga   1320
accgctaaac tgacaacctg gttaggcaag cagctcggga tactaggaaa aagttggaa    1380
aacaagagta agacgtggtt tggagcatac gctgcttccc cttactgtga tgtcgatcgc   1440
aaaattggct acatatggta tacaaaaaat tgcacccctg cctgcttacc caagaacaca   1500
aaaattgtcg gccctgggaa atttggcacc aatgcagagg acggcaagat attacatgag   1560
atgggggtc acttgtcgga ggtactacta cttctttag tggtgctgtc cgacttcgca    1620
ccggaaacag ctagtgtaat gtacctaatc ctacattttt ccatcccaca aagtcacgtt   1680
gatgtaatgg attgtgataa gaccccagttg aacctcacag tggagctgac aacagctgaa   1740
gtaataccag ggtcggtctg gaatctaggc aaatatgtat gtataagacc aaattggtgg   1800
ccttatgaga caactgtagt gttggcattt gaagaggtga gccaggtggt gaagttagtg   1860
ttgagggcac tcagagattt aacacgcatt tggaacgctg caacaactac tgcttttta    1920
gtatgccttg ttaagatagt caggggccca gatggtacag ggcattctgt ggctactatt   1980
gataacaggg gtacaagggc acttggattg caaacctgaa ttctcgtatg ccatagcaaa   2040
ggacgaaaga attggtcaac tgggggctga aggccttacc accacttgga aggaatactc   2100
acctggaatg aagctggaag acacaatggt cattgcttgg tgcgaagatg ggaagttaat   2160
gtacctccaa agatgcacga gagaaaccag atatctcgca atcttgcata caagagcctt   2220
gccgaccagt gtggtattca aaaaactctt tgatgggcga agcaagagg atgtagtcga    2280
aatgaacgac aactttgaat ttggactctg cccatgtgat gccaaaccca agtaagagg    2340
gaagttcaat acaacgctgc tgaacggacc ggccttccag atggtatgcc cataggatg    2400
gacagggact gtaagctgta cgtcattcaa tatggacacc ttagccacaa ctgtggtacg   2460
gacatataga aggtctaaac cattccctca taggcaaggc tgtatcaccc aaaagaatct   2520
ggggggaggat ctccataact gcatccttgg aggaaattgg acttgtgtgc ctggagcca   2580
actactatac aaagggggct ctattgaatc ttgcaagtgg tgtggctatc aatttaaaga   2640
gagtgaggga ctaccacact acccccattgg caagtgtaaa ttggagaacg agactggtta   2700
caggctagta gacagtacct cttgcaatag agaaggtgtg gccatagtac cacaagggac   2760
```

-continued

| | | | | |
|---|---|---|---|---|
| attaaagtgc | aagataggaa | aaacaactgt | acaggtcata | gctatggata ccaaactcgg | 2820 |
| acctatgcct | tgcagaccat | atgaaatcat | atcaagtgag | gggcctgtag aaaagacagc | 2880 |
| gtgtactttc | aactcacacta | agacattaaa | aaataagtat | tttgagccca gagacagcta | 2940 |
| ctttcagcaa | tacatgctaa | aaggagagta | tcaatactgg | tttgacctgg aggtgactga | 3000 |
| ccatcaccgg | gattacttcg | ctgagtccat | attagtggtg | gtagtagccc tcttgggtgg | 3060 |
| cagatatgta | ctttggttac | tggttacata | catggtctta | tcagaacaga aggccttagg | 3120 |
| gattcagtat | ggatcagggg | aagtggtgat | gatgggcaac | ttgctaaccc ataacaatat | 3180 |
| tgaagtggtg | acatacttct | tgctgctgta | cctactgctg | agggaggaga gcgtaaagaa | 3240 |
| gtgggtctta | ctcttatacc | acatcttagt | ggtacaccca | atcaaatctg taattgtgat | 3300 |
| cctactgatg | attggggatg | tggtaaaggc | cgattcaggg | ggccaagagt acttggggaa | 3360 |
| aatagacctc | tgttttacaa | cagtagtact | aatcgtcata | ggtttaatca tagctaggcg | 3420 |
| tgacccaact | atagtgccac | tggtaacaat | aatggcagca | ctgagggtca ctgaactgac | 3480 |
| ccaccagcct | ggagttgaca | tcgctgtggc | ggtcatgact | ataaccctac tgatggttag | 3540 |
| ctatgtgaca | gattatttta | gatataaaaa | atggttacag | tgcattctca gcctggtatc | 3600 |
| tgcggtgttc | ttgataagaa | gcctaatata | cctaggtaga | atcgagatgc cagaggtaac | 3660 |
| tatcccaaac | tggagaccac | taactttaat | actattatat | ttgatctcaa caacaattgt | 3720 |
| aacgaggtgg | aaggttgacg | tggctggcct | attgttgcaa | tgtgtgccta tcttattgct | 3780 |
| ggtcacaacc | ttgtgggccg | acttcttaac | cctaatactg | atcctgccta cctatgaatt | 3840 |
| ggttaaatta | tactatctga | aaactgttag | gactgataca | gaaagaagtt ggctaggggg | 3900 |
| gatagactat | acaagagttg | actccatcta | cgacgttgat | gagagtggag agggcgtata | 3960 |
| tctttttcca | tcaaggcaga | aagcacaggg | gaatttttct | atactcttgc cccttatcaa | 4020 |
| agcaacactg | ataagttgcg | tcagcagtaa | atggcagcta | atatacatga gttacttaac | 4080 |
| tttggacttt | atgtactaca | tgcacaggaa | agttatagaa | gagatctcag gaggtaccaa | 4140 |
| cataatatcc | aggttagtgg | cagcactcat | agagctgaac | tggtccatgg aagaagagga | 4200 |
| gagcaaaggc | ttaaagaagt | tttatctatt | gtctggaagg | ttgagaaacc taataataaa | 4260 |
| acataaggta | aggaatgaga | ccgtggcttc | ttggtacggg | gaggaggaag tctacggtat | 4320 |
| gccaaagatc | atgactataa | tcaaggccag | tacactgagt | aagagcaggc actgcataat | 4380 |
| atgcactgta | tgtgagggcc | gagagtggaa | aggtggcacc | tgcccaaaat gtggacgcca | 4440 |
| tgggaagccg | ataacgtgtg | ggatgtcgct | agcagatttt | gaagaaagac actataaaag | 4500 |
| aatctttata | agggaaggca | actttgaggg | tatgtgcagc | cgatgccagg gaaagcatag | 4560 |
| gaggtttgaa | atggaccggg | aacctaagag | tgccagatac | tgtgctgagt gtaataggct | 4620 |
| gcatcctgct | gaggaaggtg | acttttgggc | agagtcgagc | atgttgggcc tcaaaatcac | 4680 |
| ctactttgcg | ctgatggatg | gaaaggtgta | tgatatcaca | gagtgggctg gatgccagcg | 4740 |
| tgtgggaatc | tccccagata | cccacagagt | cccttgtcac | atctcatttg gttcacggat | 4800 |
| gcctttcagg | caggaataca | atggctttgt | acaatatacc | gctaggggggc aactatttct | 4860 |
| gagaaacttg | cccgtactgg | caactaaagt | aaaaatgctc | atggtaggca accttggaga | 4920 |
| agaaattggt | aatctggaac | atcttgggtg | gatcctaagg | gggcctgccg tgtgtaagaa | 4980 |
| gatcacagag | cacgaaaaat | gccacattaa | tatactggat | aaactaaccg cattttttcgg | 5040 |
| gatcatgcca | ggggggacta | cacccagagc | cccggtgagg | ttccctacga gcttactaaa | 5100 |
| agtgaggagg | ggtctggaga | ctgcctgggc | ttacacacac | caaggcggga taagttcagt | 5160 |

```
cgaccatgta accgccggaa aagatctact ggtctgtgac agcatgggac gaactagagt   5220
ggtttgccaa agcaacaaca ggttgaccga tgagacagag tatggcgtca agactgactc   5280
agggtgccca gacggtgcca gatgttatgt gttaaatcca gaggccgtta acatatcagg   5340
atccaaaggg gcagtcgttc acctccaaaa gacaggtgga gaattcacgt gtgtcaccgc   5400
atcaggcaca ccggctttct tcgacctaaa aacttgaaa ggatggtcag gcttgcctat   5460
atttgaagcc tccagcggga gggtggttgg cagagtcaaa gtagggaaga atgaagagtc   5520
taaacctaca aaataatga gtggaatcca gaccgtctca aaaaacagag cagacctgac   5580
cgagatggtc aagaagataa ccagcatgaa caggggagag ttcaagcaga ttactttggc   5640
aacaggggca ggcaaaacca cagaactccc aaaagcagtt atagaggaga taggaagaca   5700
caagagagta ttagttctta taccattaag ggcagcggga gagtcagtct accagtatat   5760
gagattgaaa cacccaagca tctcttttaa cctaaggata ggggacatga agaggggga   5820 catggcaacc gggataacct atgcatcata cgggtacttc tgccaaatgc ctcaaccaaa   5880
gctcagagct gctatggtag aatactcata catattctta gatgaatacc attgtgccac   5940
tcctgaacaa ctggcaatta tcgggaagat ccacagattt tcagagagta taagggttgt   6000
cgccatgact gccacgccag cagggtcggt gaccacaaca ggtcaaaagc acccaataga   6060
ggaattcata gccccgagg taatgaaagg ggaggatctt ggtagtcagt tccttgatat   6120
agcagggtta aaaataccag tggatgagat gaaaggcaat atgttggttt ttgtaccaac   6180
gagaaacatg gcagtagagg tagcaaagaa gctaaaagct aagggctata actctggata   6240
ctattacagt ggagaggatc cagccaatct gagagttgtg acatcacaat cccctatgt   6300 aatcgtggct acaaatgcta ttgaatcagg agtgacacta ccagatttgg acacggttat   6360
agacacgggg ttgaaatgtg aaaagagggt gagggtatca tcaaagatac ccttcatcgt   6420
aacaggcctt aagaggatgg ccgtgactgt gggtgagcag gcgcagcgta ggggcagagt   6480
aggtagagtg aaacccggga ggtattatag gagccaggaa acagcaacag gtcaaaggga   6540
ctaccactat gacctcttgc aggcacaaag atacggggatt gaggatggaa tcaacgtgac   6600
gaaatccttt agggagatga attacgattg gagcctatac gaggaggaca gcctactaat   6660
aacccagctg gaaatactaa ataatcact catctcagaa gacttgccag ccgctgttaa   6720
gaacataatg gccaggactg atcacccaga gccaatccaa cttgcataca acagctatga   6780
agtccaggtc ccggtcctat tcccaaaaat aaggaatgga gaagtcacag acacctacga   6840
aaattactcg tttctaaatg ccagaaagtt agggggaggat gtgcccgtgt atatctacgc   6900
tactgaagat gaggatctgg cagttgacct cttagggcta gactggcctg atcctgggaa   6960
ccagcaggta gtggagactg gtaaagcact gaagcaagtg accgggttgt cctcggctga   7020
aaatgcccta ctagtggctt tatttgggta tgtgggttac caggctctct caaagaggca   7080
tgtcccaatg ataacagaca tatatacccat cgaggaccag agactagaag acaccaccca   7140
cctccagtat gcacccaacg ccataaaaac cgatgggaca gagactgaac tgaaagaact   7200
ggcgtcgggt gacgtggaaa aaatcatggg agccatttca gattatgcag ctgggggact   7260
ggagtttgtt aaatcccaag cagaaagat aaaaacagct cctttgttta agaaaacgc   7320 agaagccgca aagggtatg tccaaaaatt cattgactca ttaattgaaa ataaagaaga   7380
aataatcaga tatggtttgt ggggaacaca cacagcacta tacaaaagca tagctgcaag   7440 actgggcat gaaacagcgt ttgccacact agtgttaaag tggctagctt ttggagggga   7500
atcagtgtca gaccacgtca agcaggcggc agttgattta gtggtctatt atgtgatgaa   7560
```

-continued

```
taagccttcc ttcccaggtg actccgagac acagcaagaa gggaggcgat tcgtcgcaag    7620
cctgttcatc tccgcactgg caacctacac atacaaaact tggaattacc acaatctctc    7680
taaagtggtg gaaccagccc tggcttacct cccctatgct accagcgcat aaaaatgtt     7740 caccccaacg cggctggaga gcgtggtgat actgagcacc acgatatata aaacatacct    7800
ctctataagg aagggaaga gtgatggatt gctgggtacg gggataagtg cagccatgga     7860
aatcctgtca caaacccag tatcggtagg tatatctgtg atgttggggg tagggcaat     7920 cgctgcgcac aacgctattg agtccagtga acagaaaagg accctactta tgaaggtgtt    7980
tgtaaagaac ttcttggatc aggctgcaac agatgagctg gtaaaagaaa acccagaaaa    8040
aattataatg gccttatttg aagcagtcca gacaattggt aaccccctga gactaatata    8100
ccacctgtat ggggtttact acaaaggttg ggaggccaag gaactatctg agaggacagc    8160
aggcagaaac ttattcacat tgataatgtt tgaagccttc gagttattag ggatggactc    8220
acaagggaaa ataaggaacc tgtccggaaa ttacattttg gatttgatat acggcctaca    8280
caagcaaatc aacagagggc tgaagaaaat ggtactgggg tgggcccctg cacccttag     8340 ttgtgactgg accctagtg acgagaggat cagattgcca acagacaact atttgagggt    8400
agaaaccagg tgcccatgtg gctatgagat gaaagctttc aaaaatgtag gtggcaaact    8460
taccaaagtg gaggagagcg ggcctttcct atgtagaaac agacctggta ggggaccagt    8520
caactacaga gtcaccaagt attacgatga caacctcaga gagataaaac cagtagcaaa    8580
gttggaagga caggtagagc actactacaa aggggtcaca gcaaaaattg actacagtaa    8640
aggaaaaatg ctcttggcca ctgacaagtg ggaggtggaa catggtgtca taaccaggtt    8700
agctaagaga tatactgggg tcgggttcaa tggtgcatac ttaggtgacg agcccaatca    8760
ccgtgctcta gtggagaggg actgtgcaac tataaccaaa aacacagtac agtttctaaa    8820
aatgaagaag gggtgtgcgt tcacctatga cctgaccatc tccaatctga ccaggctcat    8880
cgaactagta cacaggaaca atcttgaaga aaggaaata cccaccgcta cggtcaccac    8940
atggctagct tacaccttcg tgaatgaaga cgtagggact ataaaaccag tactaggaga    9000
gagagtaatc cccgaccctg tagttgatat caatttacaa ccagaggtgc aagtggacac    9060
gtcagaggtt gggatcacaa taattggaag ggaaacccctg atgacaacgg gagtgacacc    9120
tgtcttggaa aaagtagagc ctgacgccag cgacaaccaa aactcggtga agatcgggtt    9180
ggatgagggt aattacccag ggcctggaat acagacacat acactaacag aagaaataca    9240
caacagggat gcgaggccct tcatcatgat cctgggctca aggaattcca tatcaaatag    9300
ggcaaagact gctagaaata taaatctgta cacaggaaat gacccccaggg aaatacgaga    9360 cttgatggct gcagggcgca tgttagtagt agcactgagg gatgtcgacc ctgagctgtc    9420
tgaaatggtc gatttcaagg ggactttttt agatagggag gccctggagg ctctaagtct    9480
cgggcaacct aaaccgaagc aggttaccaa ggaagctgtt aggaatttga tagaacagaa    9540 aaagatgtg gagatcccta actggtttgc atcagatgac ccagtatttc tggaagtggc    9600
cttaaaaaat gataagtact acttagtagg agatgttgga gagctaaaag atcaagctaa    9660
agcacttggg gccacggatc agacaagaat tataaaggag gtaggctcaa ggacgtatgc    9720
catgaagcta tctagctggt tcctcaaggc atcaaacaaa cagatgagtt taactccact    9780
gtttgaggaa ttgttgctac ggtgcccacc tgcaactaag agcaataagg gcacatggc     9840 atcagcttac caattggcac agggtaactg ggagcccctc ggttgcgggg tgcacctagg    9900 tacaataccca gccagaaggg tgaagataca cccatatgaa gcttacctga gttgaaaga    9960
```

```
tttcatagaa gaagaagaga agaaacctag ggttaaggat acagtaataa gagagcacaa    10020
caaatggata cttaaaaaaa taaggtttca aggaaacctc aacaccaaga aaatgctcaa    10080
cccagggaaa ctatctgaac agttggacag ggaggggcgc aagaggaaca tctacaacca    10140
ccagattggt actataatgt caagtgcagg cataaggctg gagaaattgc caatagtgag    10200
ggcccaaacc gacaccaaaa cctttcatga ggcaataaga gataagatag acaagagtga    10260
aaaccggcaa atccagaat tgcacaacaa attgttggag attttccaca cgatagccca     10320
acccacccctg aaacacacct acggtgaggt gacgtgggag caacttgagg cggggtaaa    10380
tagaaagggg gcagcaggct tcctggagaa gaagaacatc ggagaagtat tggattcaga    10440
aaagcacctg gtagaacaat tggtcaggga tctgaaggcc gggagaaaga taaaatatta    10500
tgaaactgca ataccaaaaa atgagaagag agatgtcagt gatgactggc aggcagggga    10560
cctggtggtt gagaagaggc caagagttat ccaatacct gaagccaaga caaggctagc     10620
catcactaag gtcatgtata actgggtgaa acagcagccc gttgtgattc caggatatga    10680
aggaaagacc cccttgttca acatctttga taaagtgaga aaggaatggg actcgttcaa    10740
tgagccagtg gccgtaagtt ttgacaccaa agcctgggac actcaagtga ctagtaagga    10800
tctgcaactt attggagaaa tccagaaata ttactataag aaggagtggc acaagttcat    10860
tgacaccatc accgaccaca tgacagaagt accagttata acagcagatg gtgaagtata    10920
tataagaaat gggcagagag ggagcggcca gccagacaca agtgctggca acagcatgtt    10980
aaatgtcctg acaatgatgt acggcttctg cgaaagcaca ggggtaccgt acaagagttt    11040
caacagggtg gcaaggatcc acgtctgtgg ggatgatggc ttcttaataa ctgaaaaagg    11100
gttaggctg aaatttgcta acaaagggat gcagattctt catgaagcag gcaaacctca     11160
gaagataacg gaagggggaaa agatgaaagt tgcctataga tttgaggata tagagttctg    11220
ttctcatacc ccagtccctg ttaggtggtc cgacaacacc agtagtcaca tggccgggag    11280
agacaccgct gtgatactat caaagatggc aacaagattg gattcaagtg gagagagggg    11340
taccacagca tatgaaaaag cggtagcctt cagtttcttg ctgatgtatt cctggaaccc    11400
gcttgttagg aggatttgcc tgttggtcct ttcgcaacag ccagagacag acccatcaaa    11460
acatgccact tattattaca aggtgatcc aataggggcc tataaagatg taataggtcg     11520
gaatctaagt gaactgaaga gaacaggctt tgagaaattg gcaaatctaa acctaagcct    11580
gtccacgttg ggggtctgga ctaagcacac aagcaaaaga ataattcagg actgtgttgc    11640
cattgggaaa gaagagggca actggctagt taagcccgac aggctgatat ccagcaaaac    11700
tggccactta tacatacctg ataaaggctt tacattacaa ggaaagcatt atgagcaact    11760
gcagctaaga acagagacaa acccggtcat ggggggttggg actgagagat acaagttagg    11820
tcccatagtc aatctgctgc tgagaaggtt gaaaattctg ctcatgacgg ccgtcggcgt    11880
cagcagctga gacaaaatgt atatattgta aataaattaa tccatgtaca tagtgtatat    11940
aaatatagtt gggaccgtcc acctcaagaa gacgacacgc ccaacacgca cagctaaaca    12000
gtagtcaaga ttatctacct caagataaca ctacatttaa tgcacacagc actttagctg    12060
tatgaggata cgcccgacgt ctatagttgg actagggaag acctctaaca gcccccgcgg    12120
atctagagga gcatgcgacg tcaggtgca cttttcgggg aaatgtgcgc ggaacccta     12180
tttgtttatt tttctaaata cattcaaata tgtatccgct catgagacaa taaccctgat    12240
aaatgcttca ataatattga aaaggaaga gtatgagtat tcaacatttc cgtgtcgccc    12300
ttattccctt ttttgcggca ttttgccttc ctgtttttgc tcacccagaa acgctggtga    12360
```

```
aagtaaaaga tgctgaagat cagttgggtg cacgagtggg ttacatcgaa ctggatctca    12420
acagcggtaa gatccttgag agttttcgcc ccgaagaacg ttttccaatg atgagcactt    12480
ttaaagttct gctatgtggc gcggtattat cccgtattga cgccgggcaa gagcaactcg    12540
gtcgccgcat acactattct cagaatgact tggttgagta ctcaccagtc acagaaaagc    12600
atcttacgga tggcatgaca gtaagagaat tatgcagtgc tgccataacc atgagtgata    12660
acactgcggc caacttactt ctgacaacga tcggaggacc gaaggagcta accgcttttt    12720
tgcacaacat gggggatcat gtaactcgcc ttgatcgttg ggaaccggag ctgaatgaag    12780
ccataccaaa cgacgagcgt gacaccacga tgcctgtagc aatggcaaca cgttgcgca    12840 aactattaac tggcgaacta cttactctag cttcccggca acaattaata gactggatgg    12900
aggcggataa agttgcagga ccacttctgc gctcggccct tccggctggc tggtttattg    12960
ctgataaatc tggagccggt gagcgtgggt ctcgcggtat cattgcagca ctggggccag    13020
atggtaagcc ctcccgtatc gtagttatct acacgacggg gagtcaggca actatggatg    13080
aacgaaatag acagatcgct gagataggtg cctcactgat taagcattgg taactgtcag    13140
accaagttta ctcatatata ctttagattg atttaaaact tcatttttaa tttaaaagga    13200
tctaggtgaa gatccttttt gataatctca tgaccaaaat cccttaacgt gagttttcgt    13260
tccactgagc gtcagacccc gtagaaaaga tcaaaggatc ttcttgagat cctttttttc    13320
tgcgcgtaat ctgctgcttg caaacaaaaa aaccaccgct accagcggtg gtttgtttgc    13380
cggatcaaga gctaccaact ctttttccga aggtaactgg cttcagcaga gcgcagatac    13440
caaatactgt ccttctagtg tagccgtagt taggccacca cttcaagaac tctgtagcac    13500
cgcctacata cctcgctctg ctaatcctgt taccagtggc tgctgccagt ggcgataagt    13560
cgtgtcttac cgggttggac tcaagacgat agttaccgga taaggcgcag cggtcgggct    13620
gaacgggggg ttcgtgcaca gcccagct tggagcgaac gacctacacc gaactgagat    13680
acctacagcg tgagctatga gaaagcgcca cgcttcccga agggagaaag gcggacaggt    13740
atccggtaag cggcagggtc ggaacaggag agcgcacgag ggagcttcca gggggaaacg    13800
cctggtatct ttatagtcct gtcgggtttc gccacctctg acttgagcgt cgatttttgt    13860
gatgctcgtc agggggggcgg agcctatgga aaaacgccag caacgcggcc ttttacggt    13920 tcctggcctt ttgctggcct tttgctcaca tgttctttcc tgcgttatcc cctgattctg    13980
tggataaccg tattaccgcc tttgagtgag ctgataccgc tcgccgcagc cgaacgaccg    14040
agcgcagcga gtcagtgagc gaggaagcgg aagagcgc                           14078
```

```
<210> SEQ ID NO 2
<211> LENGTH: 20
<212> TYPE: DNA
<213> ORGANISM: Artificial Sequence
<220> FEATURE:
<223> OTHER INFORMATION: :

<400> SEQUENCE: 2
aaaggtctcg agatgccacg                                                     20

<210> SEQ ID NO 3
<211> LENGTH: 39
<212> TYPE: DNA
<213> ORGANISM: Artificial Sequence
<220> FEATURE:
<223> OTHER INFORMATION: :
```

```
<400> SEQUENCE: 3
gtctgacatg tgccatgtac agcagagatt tttagtagc                       39

<210> SEQ ID NO 4
<211> LENGTH: 29
<212> TYPE: DNA
<213> ORGANISM: Artificial Sequence
<220> FEATURE:
<223> OTHER INFORMATION: :

<400> SEQUENCE: 4
cacatgtcag acacgaaaga agagggagc                                  29

<210> SEQ ID NO 5
<211> LENGTH: 22
<212> TYPE: DNA
<213> ORGANISM: Artificial Sequence
<220> FEATURE:
<223> OTHER INFORMATION: :

<400> SEQUENCE: 5
caggtttgca atccaagtgc cc                                         22

<210> SEQ ID NO 6
<211> LENGTH: 20
<212> TYPE: DNA
<213> ORGANISM: Artificial Sequence
<220> FEATURE:
<223> OTHER INFORMATION: :

<400> SEQUENCE: 6
ggagcatacg ctgcttcccc                                            20

<210> SEQ ID NO 7
<211> LENGTH: 21
<212> TYPE: DNA
<213> ORGANISM: Artificial Sequence
<220> FEATURE:
<223> OTHER INFORMATION: :

<400> SEQUENCE: 7
gccttgccta tgagggaatg g                                          21

<210> SEQ ID NO 8
<211> LENGTH: 19
<212> TYPE: DNA
<213> ORGANISM: Artificial Sequence
<220> FEATURE:
<223> OTHER INFORMATION: :

<400> SEQUENCE: 8
cacttgcatc catcatacc                                             19

<210> SEQ ID NO 9
<211> LENGTH: 27
<212> TYPE: DNA
<213> ORGANISM: Bovine Viral Diarrhea Virus

<400> SEQUENCE: 9
tgtacatggc acatgtcaga cacgaaa                                    27
```

ATTENUATED FORMS OF BOVINE VIRAL DIARRHEA VIRUS

CROSS REFERENCE TO RELATED APPLICATIONS

This application is a divisional application of U.S. Ser. No. 09/702,330, filed on Oct. 31, 2000, now U.S. Pat. No. 6,410,032, which is a divisional application of U.S. Ser. No. 09/433,262, filed Nov. 4, 1999, now U.S. Pat. No. 6,168,942, which claims benefit of priority to U.S. Ser. No. 60/107,908, filed Nov. 10, 1998, all of which are incorporated herein by reference.

FIELD OF THE INVENTION

The present invention is directed to methods of producing an attenuated form of bovine viral diarrhea (BVD) virus by inactivating a specific gene in the viral genome. The attenuated virus, or the mutated viral genome, can be used to produce antibody against BVD virus or in vaccines designed to protect cattle from viral infection.

BACKGROUND OF THE INVENTION

Bovine viral diarrhea (BVD) virus is classified in the pestivirus genus and Flaviviridae family. It is closely related to viruses causing border disease in sheep and classical swine fever. Infected cattle exhibit "mucosal disease" which is characterized by elevated temperature, diarrhea, coughing and ulcerations of the alimentary mucosa (Olafson, et al., *Cornell Vet.* 36:205–213 (1946); Ramsey, et al, *North Am. Vet.* 34:629–633 (1953)). The BVD virus is capable of crossing the placenta of pregnant, cattle and may result in the birth of persistently infected (PI) calves (Malmquist, *J. Am. Vet. Med. Assoc.* 152:763–768 (1968); Ross, et al, *J. Am. Vet. Med. Assoc.* 188:618–619 (1986)). These calves are immunotolerant to the virus and persistently viremic for the rest of their lives. They provide a source for outbreaks of mucosal disease (Liess, et al., *Dtsch. Tieraerztl. Wschr.* 81:481–487 (1974)) and are highly predisposed to infection with microorganisms causing diseases such as pneumonia or enteric disease (Barber, et al, *Vet. Rec.* 117:459–464 (1985)).

BVD viruses are classified as having one of two different biotypes. Those of the "cp" biotype induce a cytopathic effect in cultured cells, whereas viruses of the "ncp" biotype do not (Gillespie, et al, *Cornell Vet.* 50:73–79 (1960)). In addition, two major genotypes (type I and II) are recognized, both of which have been shown to cause a variety of clinical syndromes (Pellerin, et al, *Virology* 203:260–268 (1994); Ridpath, et al., *Virology* 205:66–74 (1994)).

The genome of the BVD virus is approximately 12.5 kb in length and contains a single open reading frame located between the 5' and 3' non-translated regions (NTRs) (Collett, et al., *Virology* .165:191–199 (1988)). A polyprotein of approximately 438 kD is translated from this open reading frame and is processed into viral structural and nonstructural proteins by cellular and viral proteases (Tautz, et al.,*J. Virol.* 71:5415–5422 (1997); Xu, et al, *J. Virol.* 71:5312–5322 (1997); Elbers, et al., *J. Virol.* 70:4131–4135 (1996); and Wiskerchen, et al., *Virology* 184:341–350 (1991)). Among the viral enzymes that participate in this processing are the proteases $N^{pro}$ and NS3. $N^{pro}$ is the first protein encoded by the viral open reading frame and cleaves itself from the rest of the synthesized polyprotein (Stark, et al, *J. Virol.* 67:7088–7093(1993); Wiskerchen, et al., *Virol.* 65:4508–4514(1991)).

Among the BVD vaccines that are currently available are those in which virus has been chemically inactivated (McClurkin, et al., *Arch. Virol.* 58:119 (1978); Fernelius, et al., *Am. J. Vet. Res.* 33:1421–1431 (1972); and Kolar, et at, *Am. J. Vet. Res.* 33:1415–1420 (1972)). These vaccines have typically required the administration of multiple doses to achieve primary immunization, provide immunity of short duration and do not protect against fetal transmission (Bolin, *Vet. Clin. North Am. Food Anim. Pract.* 11:615–625 (1995)). In sheep, a subunit vaccine based upon a purified E2 protein has been reported (Bruschke, et al., *Vaccine* 15:1940–1945 (1997)). Unfortunately, only one such vaccine appears to protect fetuses from infection and this protection is limited to one strain of homologous virus. There is no correlation between antibody titers and protection from viral infection.

In addition, modified live virus (MLV) vaccines have been produced using BVD virus that has been attenuated by repeated passage in bovine or porcine cells (Coggins, et al., *Cornell Vet.* 51:539 (1961); and Phillips, et al, *Am. J. Vet. Res.* 36:135 (1975)) or by chemically induced mutations that confer a temperature-sensitive phenotype on the virus (Lobmann, et al, *Am. J. Vet. Res.* 45:2498 (1984); and Lobmann, et al, *Am. J. Vet. Res.* 47:557–561 (1986)). A single dose of MLV vaccine has proven sufficient for immunization and the duration of immunity can extend for years in vaccinated cattle (Coria, et al., *Can. J. Con. Med.* 42:239 (1978)). In addition, cross-protection has been reported from calves vaccinated with MLV-type vaccines (Martin, et al., In *Proceedings of the Conference Res. Workers' Anim. Dis.,* 75:183 (1994)). However, safety considerations, such as possible fetal transmission of the virus, have been a major concern with respect to the use of these vaccines (Bolin, *Vet. Clin. North Am. Food Anim. Pract.* 11:615–625 (1995)).

A clear need exists for new and effective vaccines to control the spread of the BVD virus. Given that the disease caused by this virus is one of the most widespread and economically important diseases of cattle, such vaccines would represent a substantial advance in livestock farming.

SUMMARY OF THE INVENTION

The present invention is based upon the discovery that attenuated forms of BVD virus can be produced by deleting or inactivating the $N^{Pro}$ protease gene. These viruses are much less infectious than their wild-type counterparts in bovine cell lines and are suitable for use in vaccines for cattle. A complete genomic sequence of one such attenuated virus is disclosed herein, and a plasmid encoding this virus, i.e., pBVDdN1, has been deposited with the American Type Culture Collection (ATCC) as ATCC No. 203354 (Deposited Oct. 28, 1998, at the American Type Culture Collection, Manassas, Va. 20110-2209. U.S.A.).

A. Compositions and Methods Based Upon the BVDdN1 Attenuated Virus

In its first aspect, the present invention is based upon the development of a specific attenuated BVD viral strain. The strain is produced by mutating a wild type viral genome to delete the $N^{pro}$ protease gene and its full-length sequence is shown in SEQ ID NO: 1 and FIG. 2, from nt 39 to nt 12116. Thus, the invention is directed to a virus having a genomic sequence comprising that shown, and preferably consisting essentially of that shown. Ordinarily, the BVD virus has a genome in the form of RNA. When cloned, this will more typically be in the form of DNA. Unless otherwise indicated, the term "nucleic acid" refers to both BVD viral DNA and RNA sequences. For convenience, sequence listing entries only show DNA sequences but the corresponding RNA sequence for each will be readily apparent to those of skill in the art The term "consisting essentially of" refers to sequences that are substantially the same as those specified both in terms of structure and function. Thus, the invention includes not only the sequences expressly depicted, but also corresponding sequences made by introducing insubstantial additions or substitutions. In particular, the invention includes degenerate nucleic acid sequences that encode the same BVD proteins as SEQ ID NO: 1. This particular sequence, i.e., SEQ ID NO: 1 from nt 39 to nt 12116, and the corresponding virus it encodes have, for convenience, been designated as the "BVDdN1" genome and virus. Virus can be present either as part of a larger preparation or in substantially purified form, i.e., in a form essentially free from any other viral types.

The invention includes host cells carrying a BVDdN1 nucleic acid molecule of the present invention. The term "host cell" is meant to include any prokaryotic cells carrying a BVDdN1 nucleic acid molecule, and any eukaryotic cells infected with the virus or otherwise carrying a EVOdN1 nucleic acid molecule. For prokaryotic cells, the STBU strain of E. coil (GibcoBRL) has been found to give the best results for propagating the plasmid, and is generally preferred. For eukaryotic cells, mammalian cells such as MDBK cells (ATCC CCL-22) (Deposited Aug. 1982, at the American Type Culture Collection, Manassas, Va. 20110–2209. U.S.A.) and RD cells (stable transformed bovine testicular cells) are generally preferred. However, other cultured cells can be used as well. The invention further includes progeny 25 virus produced in such host cells.

The BVDdN1 virus can be used to induce the production of antibody by infecting an animal at an effective dosage, i.e., at a dosage high enough to provoke antibody production. The antibodies can be made in any of the animals normally used for this purpose (such as mice, rabbits, goats, or sheep) but, preferably, antibodies will be made in cattle. The term "antibody to BVD virus" as used herein refers to antibodies that react preferentially in the sense of having at least a 100-fold greater affinity for a strain of BVD virus than for any other, non-BVD virus. Although not preferred, virus can be further inactivated prior to administration to an animal using chemical treatments involving agents such as formalin, paraformaldehyde, phenol, lactopropionate, psoralens, platinum complexes, ozone or other viricidal agents. Antibodies made by these procedures are themselves included within the scope of the invention and can be isolated using techniques that are well known in the art (see e.g., Harlow, et al., *Antibodies: A Laboratory Manual*, Cold Spring Harbor Laboratory, N.Y. (1988)). The antibodies can be used, inter alia, in methods designed to detect the presence of BVD in biological or laboratory samples.

In another aspect, the invention is directed to a vaccine comprising the BVDdN1 virus and a veterinarily acceptable carrier. This vaccine can include any of the adjuvants and other agents typically used in such preparations. An immune response can be induced in cattle by administering the vaccine at a dosage sufficient to induce protective immunity against subsequent challenge with BVD virus. Typically, the vaccine will be administered parenterally, but other routes of administration are compatible with the invention as well. If necessary, two or more inoculations can be given at regular intervals of, for example, two to eight weeks. Standard procedures well known in the art can be used to optimize immunization protocols.

B. Compositions and Methods Based Upon BVDdN1 Genomic Nucleic Acid

Recent work has demonstrated that it is possible to prepare effective vaccines by injecting animals with nucleic acids encoding immunogens. Methods for making and administering these "DNA vaccines" have been described in detail (see e.g., U.S. Pat. Nos. 5,589,466; 5,580,859; and 5,703,055) and can be applied to BVDdN1 genomic nucleic acid. Thus, in another aspect, the present invention is directed to a nucleic acid molecule, preferably in substantially purified form, comprising the sequence of SEQ ID NO: 1, from nt 39 to nt 12116, or a degenerate variant thereof. In a preferred embodiment, the present invention is directed to a nucleic acid molecule, preferably in substantially purified form, consisting essentially of the sequence of SEQ ID NO: 1, from nt 39 to nt 12116. As used herein, "substantially purified" refers to a desired product that is essentially free from contaminating materials. For example, a "substantially purified" nucleic acid molecule would be essentially free from other contaminating nucleic acid molecules and typically comprise at least 85 wt % of the nucleic acid molecules in a sample, with greater percentages being preferred. One method for determining the purity of a nucleic acid is by electrophoresing a preparation in a matrix such as polyacrylamide or agarose. Purity is evidenced by the appearance of a single band after staining. Other methods for assessing purity include chromatography and analytical centrifugation.

The BVDdN1 genomic nucleic acid can be incorporated into a vector as a distinct coding element The phrase "distinct coding element" refers to the portion of the vector that is translated into viral polypeptide and, eventually, virus. It is distinct in the sense that it does not include any other translated elements that would substantially alter the BVDdN1 product. This vector, or the BVDdN1 nucleic acid itself, can be used to transfect a host cell in order to produce progeny attenuated virus.

The invention also includes methods of inducing the production of antibody to BVD virus by injecting the BVDdN1 nucleic acid, or a vector containing this nucleic acid, directly into an animal. Any animal capable of making antibody can be used, but cattle are generally preferred. Antibody made in this way is part of the invention and can be purified from animals and used, for example, in assays designed to detect the presence of BVD virus in culture medium or biological fluid.

Vaccines for administration to cattle can be prepared based upon the BVDdN1 genomic nucleic acid (see references cited supra), in combination with a veterinarily acceptable carrier, and used in immunization protocols optimized for inducing protective immunity against subsequent viral infection.

C. Methods of Mutating Wild Type BVD Genomes

In a more general sense, the present invention is directed to a method of modifying a genome from a substantially purified wild type BVD virus in such a manner as to make it suitable for use in a vaccine. The term "substantially purified" as used in this context refers to a viral preparation consisting, preferably, of a single strain of BVD virus with no other types of virus being present. The main distinguishing feature of the procedure is that the genomic nucleic acid is mutated to inactivate the $N^{pro}$ protease gene. In this context, a gene is considered to be inactivated either if no product is made (for example, the gene is deleted), or a product is made that can no longer carry out its normal biological function (e.g., proteolytic cleavage), or a product is made that carries out its normal biological function but at a significantly reduced rate. Any method that results in the inactivation of the $N^{pro}$ protease can be used. For example, genomic RNA can be isolated from the wild type BVD virus, reverse transcribed to form cDNA and then cloned using standard procedures. Mutations can then be introduced into the N$^{pro}$ protease gene by procedures such as the polymerase chain reaction (PCR), site directed mutagenesis, by synthesizing and ligating DNA fragments in such a manner that N$^{pro}$ is partially or completely eliminated, or by random mutagenesis techniques including, e.g., exposure to a chemical mutagen or radiation as known in the art, or by a combination of such procedures.

Once the BVD viral genome has been modified so that the N$^{pro}$ gene is inactivated, it can be cloned into an appropriate vector and produced in large amounts. As discussed above, vectors should include the BVD sequence as a distinct element with a sequence comprising, or consisting essentially of, that of the mutated wild type virus. Either the mutated BVD genome or the vector comprising the genome can be transformed or transfected into a host cell for the purpose of making either large amounts of viral nucleic acid or virus itself.

As discussed above in connection with the BVDdN1 genomic DNA, antibody to BVD virus can be produced in an animal by administering any wild type BVD viral genome that has been mutated in the manner discussed above. In general, it is preferred that antibody production take place in cattle, but other animals can be used as well.

Vaccines incorporating the mutated BVD genomic nucleic acid can be produced and used to induce an immune response in cattle using standard DNA immunization procedures (e.g., those discussed in U.S. Pat. Nos. 5,589,466; 5,580,859; and 5,703,055). The vaccines, antibodies, and nucleic acids made by the methods discussed herein are all part of the present invention.

D. Methods of Making Attenuated BVD Virus

It has been discovered that when the nucleic acid of a BVD virus is mutated so as to inactivate the N$^{pro}$ protease gene, an attenuated virus is produced that is much less infectious in cell culture. The relatively slow replication of these attenuated viruses allows animals to marshal their immunological defenses in a way that is not possible for a rapidly propagating wild type virus. Thus, the methods for producing a mutated viral genome discussed above for BVDdN1 lead directly to a general method for attenuating BVD virus so as to make it suitable for use in a vaccine. In general, the procedure involves isolating a wild type BVD virus; cloning its genomic nucleic acid; mutating the cloned nucleic acid so as to inactivate the N$^{pro}$ protease gene; and then transforming or transfecting the mutated nucleic acid into a host to produce the attenuated virus. Although any of the methods discussed above for producing mutations can be used, the preferred method will be to delete all or part of the N$^{pro}$ protease gene.

The present invention encompasses not only methods for making attenuated virus, but also the virus itself, host cells infected with the virus and progeny virus produced by these host cells. Antibody can be made to the attenuated BVD virus by infecting animals, preferably cattle, at an effective dosage. Antibodies made in this manner are part of the invention and can be isolated and used in diagnostic procedures, or for detecting the presence of BVD in cell culture.

As discussed in connection with the BVDdN1 virus, attenuated virus characterized by an inactivated N$^{pro}$ protease gene can be incorporated into vaccines and used to induce an immune response in cattle. Dosages and immunization protocols can be optimized so that inoculation of animals results in protective immunity against subsequent viral challenge.

BRIEF DESCRIPTION OF THE DRAWINGS

FIG. 2 (panels A–W). The complete nucleotide sequence of plasmid pBVDdN1 is shown. The genomic sequence of BVDdN1 is represented by nucleotides 39 to 12,116 (SEQ ID NO: 1).

DETAILED DESCRIPTION OF THE INVENTION

Figure 1:
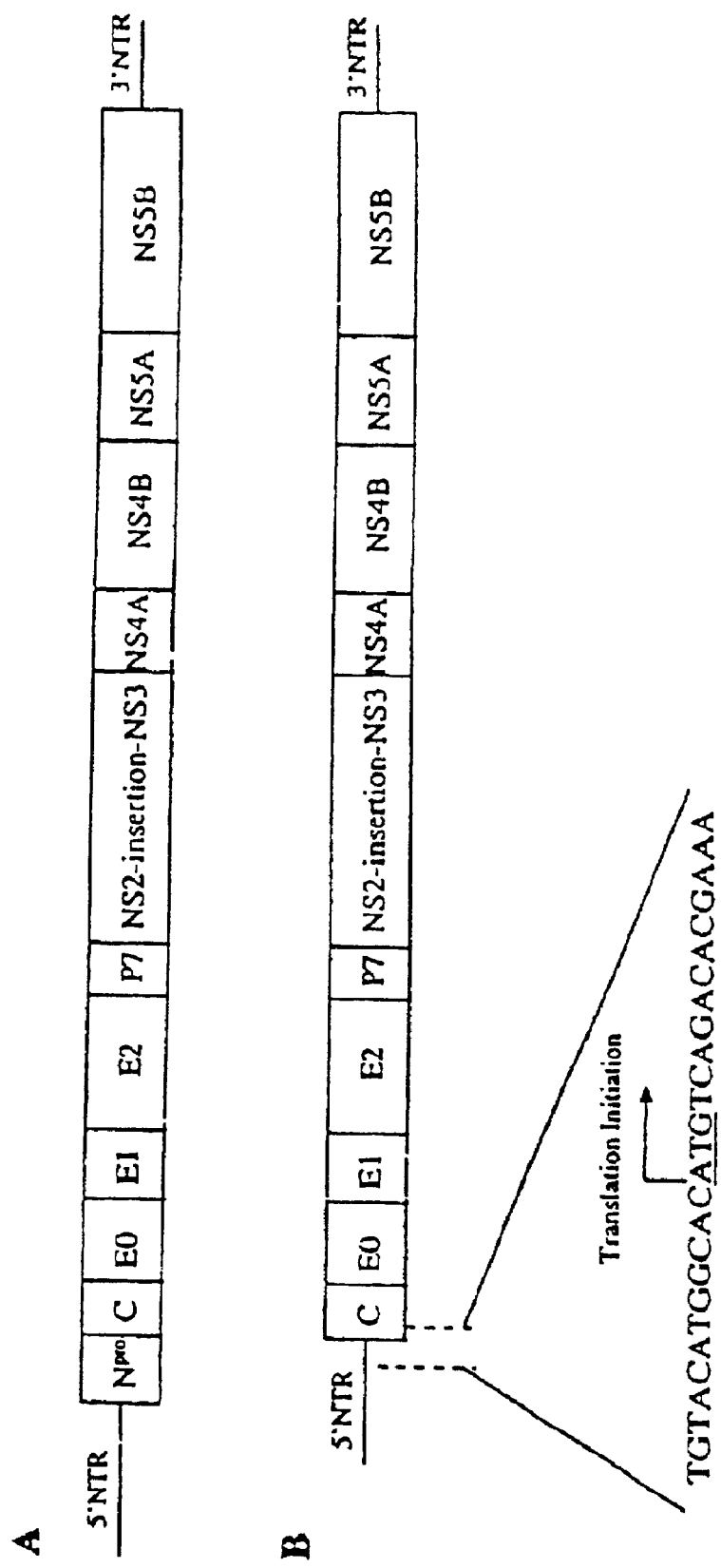
FIG. 1 (panels A and B): Panel A shows a schematic representation of the plasmid pVVNADL. This plasmid was mutated to delete the first gene in the open reading frame, i.e., N$^{pro}$ protease. The resulting mutated plasmid product, pBVDdN1, is shown schematically in panel B. Several other gene regions are also shown in FIG. 1. C represents a gene encoding a structural core protein that packages genomic RNA and forms the viral virion. This is followed by genes encoding three envelope glycoproteins—E0, E1 and E2. P7 encodes a nonstructural protein with an unknown function and is followed by a region designated as "NS2-insertion-NS3." NS2 encodes a highly hydrophobic protein with a zinc finger motif. NS3 is hydrophilic and is a marker of cytopathic BVD virus. Replication of ncp virus in an infected animal can convert the virus into the cp biotype through genetic recombination involving the insertion of an extra viral or cellular RNA sequence between the NS2 and NS3 coding regions. As a result of the recombination, free NS2 and NS3 protein are released. The latter, i.e., NS3, is a protease responsible for most of the nonstructural protein processing that takes place. NS4A is located next to NS3 and is known to encode a cofactor for NS3 protease activity. Following NS4A, there are two genes encoding viral proteins, NS4B and NS5A, with unknown functions. The last gene, NS5B, encodes an RNA-dependent RNA polymerase and is responsible for viral replication. The nucleotide sequence (SEQ ID NO: 9) shown in panel B is the sequence surrounding the initiation codon of pBVDdN1.

A. Production of BVDdN1 and Nucleic Acid Encoding the Virus

The present invention is directed to a BVD virus that has been attenuated by the deletion of the N$^{pro}$ protease gene. The virus has been designated as BVDdN1 and, as suggested by the term "attenuated," it has been found to replicate at a much slower rate in susceptible cell lines (e.g., bovine testicular cell lines (RD), or bovine kidney cell lines (MDBK)) than its wind type counterpart in vivo. In addition, BVDdN1 does not cause productive infection in embryonic bovine trachea cells (EBTr) or bovine turbinate cells (BT-2), which can be contrasted with the productive infection that occurs following infection with wild type virus. The slow growth of BVDdN1 virus in several different bovine cell lines suggests broad tissue tropism attenuation in animals. BVDdN1 is genetically stable, as the N$^{pro}$ deletion is maintained following up to 10 passages in bovine RD cells. Although the genome of the natural virus consists of RNA, this can be reverse transcribed into DNA and cloned. It will be understood that references made herein to nucleic acid and BVD viral sequences encompass both the reverse-transcribed DNA sequences derived from the viral RNA sequences, and the corresponding RNA itself.

The complete nucleotide sequence of the BVDdN1 viral genome is shown in SEQ ID NO: 1, from nt 39 to nt 12116. It will be understood that the invention includes not only viral genomes having the exact sequence shown, but also other sequences that do not differ substantially in terms of structure or function, including, e.g., sequences that encode the same BVD proteins as SEQ ID NO: 1 as based on the degeneracy of the genetic code. In addition, e.g., it is well known that techniques such as site-directed mutagenesis can be used to introduce variations into the structure of nucleic acids. Mutations in the BVD virus nucleic acid sequence introduced by this or some similar method, or alternatively by random mutagenesis as known in the art, are encompassed by the invention, provided that at least one major biological characteristic of the resulting virus remains substantially the same as that of the virus from which it was derived. In particular, mutations that do not substantially alter the characteristics of BVDdN1 with respect to infectivity fall within the scope of the invention.

The mutated BVDdN1 nucleic acid, was derived from a National Animal Disease Laboratory (NADL) strain of BVD obtained from the American Type Culture Collection (VR-534). This was incorporated into a vector and the full length $N^{pro}$ protease gene was deleted by selective PCR and religation as described in the Examples section below. Although this procedure can be used to obtain the viral genome, and ultimately the virus itself, a plasmid containing the complete BVDdN1 genomic sequence; designated as pBVDdN1, has been deposited as ATCC No. 203354, and this represents the preferred source for isolation procedures. Standard methodology can be used to propagate and purify the plasmid, and transfect it into host cells capable of supporting virus production. The preferred prokaryotic host cell for plasmid propagation is *E. coli* STBL2 cells (available from GibcoBRL), but other cell types can also be used. The virus can be produced in eukaryotic cells, such as RD or MDBK cells, isolated therefrom in highly purified form using known separation techniques such as sucrose gradient centrifugation, and used in vaccines or to generate antibodies. Alternatively, plasmid can be used to isolate the BVDdN1 genomic sequence and this can be used directly in generating antibodies or in vaccines.

B. The Making of Other Attenuated BVD Viral Strains

The same basic procedures used for generating BVDdN1 virus and genomic nucleic acid can be used in conjunction with other wild type strains of BVD. In each case, the wild type virus is isolated and attenuation is accomplished by inactivating the $N^{pro}$ protease gene. This can preferably be accomplished by deleting the entire gene using a PCR-based strategy as discussed herein for BVDdN1. However, other methods for inactivating the gene, e.g., by deleting a portion of the sequence or introducing mutations randomly or at specific sites, can also be used. In all cases, the objective is to produce a mutated virus that proliferates at a slow rate after infection. As discussed in the Examples section, infectivity for the virus can be determined in vitro by performing immunohistochemistry using a monoclonal antibody specific for BVD virus.

C. Generation of Antibodies to Attenuated BVD Virus

Antibodies to BVD virus can be produced in any of the animals typically used for antibody production, including mice, rabbits, etc. However, it is preferred that the antibodies be produced in cattle. Compositions containing the virus can be administered to the animals by any route, but typically animals will be injected intramuscularly, subcutaneously or intravenously. Generally, the virus preparation will include an adjuvant, e.g. Freund's complete or incomplete adjuvant. Appropriate preparations for injection, injection schedules and the like are well known in the art and can be employed (see, e.g., Harlow et al., *Antibodies, A Laboratory Manual*, Cold Spring Harbor Laboratory, N.Y. (1988); Klein, *Immunology: The Science of Self-Nonself Discrimination* (1982)). Monoclonal antibodies can also be prepared using standard procedures (Kennett et al., *Monoclonal Antibodies and Hybridomas: A New Dimension in Biological Analyses* (1980); Campbell, "Monoclonal Antibody Technology" in *Laboratory Techniques in Biochemistry and Molecular Biology* (1984)).

Antibodies or fragments of antibodies reacting with specificity to BVD virus (i.e., having at least a 100-fold greater affinity for BVD than for any other type of virus) can be used in any of a variety of immunoassays. For example, the antibodies can be used to detect BVD virus in radioimmunoassays or immunometric assays, also known as "two-site" or "sandwich" assays (see Chard, "An Introduction to Radioimmune Assay and Related Techniques," in *Laboratory Techniques in Biochemistry and Molecular Biology*, North Holland Publishing Co., N.Y. (1978)). In a typical immunometric assay, a quantity of unlabeled antibody is bound to a solid support that is insoluble in the fluid being tested, e.g., blood, lymph, cellular extracts, etc. After the initial binding of antigen to immobilized antibody, a quantity of detectably labeled second antibody (which may or may not be the same as the first) is added to permit detection and/or quantitation of antigen (see, e.g., *Radioimmune Assay Methods*, Kirkham et al. ed., pp. 199–206; E & S Livingstone Edinburgh (1970)). Many variations of these types of assays are known in the art and can be employed for the detection of BVD virus.

D. Conventional Vaccines and Vaccination Procedures

Vaccines and vaccination procedures employing BVD virus have been discussed in a number of references (see, e.g., Fernelius et al, *Am. J. Vet. Res.* 33:1421–1431 (1972); Kolar et al., *Am. J. Vet. Res.* 33:1415–1420 (1972); McClurkin et al, *Arch. Virol.* 58:119 (1978); Coggins et al., *Cornell Vet.* 51:539 (1961); Phillips et al, *Am. J. Vet. Res.* 36:135 (1975); Lobmann et al, *Am. J. Vet. Res.* 45:2498 (1984); Coria et al, *Can. J. Comp. Med.* 42:239 (1978); Martin et al in *Proceedings of the Conference Res. Workers Anim. Dis.* 75:183 (1994); and U.S. Pat. No. 4,618,493). Typically, a vaccine will contain between about $1\times10^6$ and about $1\times10^8$ virus particles, with a veterinarily acceptable carrier, in a volume of between 0.5 and 5 ml. Formulation can take place using methods such as those described in *Remington's Pharmaceutical Sciences* (Mack Publishing Co., Easton, Pa. 16th ed. 1982)). The invention is compatible with various excipients and adjuvants, and these can be incorporated into preparations as desired. For example, vaccine compositions of the present invention can be formulated following accepted convention using standard buffers, carriers, stabilizers, diluents, preservatives, and solubilizers, and can also be formulated to facilitate sustained release. Diluents can include water, saline, dextrose, ethanol, glycerol, and the like. Additives for isotonicity can include sodium chloride, dextrose, mannitol, sorbitol, and lactose, among others. Stabilizers include albumin, among others. Non-limiting examples of adjuvants include the RIBI adjuvant system (Ribi Inc.), alum, aluminum hydroxide gel, oil-in-water emulsions, water-in-oil emulsions such as, e.g., Freund's complete and incomplete adjuvants, Block co polymer (CytRx, Atlanta Ga.), SAF-M (Chiron, Emeryville Calif.), AMPHIGEN® adjuvant, saponin, Quil A, QS-21 (Cambridge Biotech Inc., Cambridge Mass.), or other saponin fractions, monophosphoryl lipid A, Avridine lipid-amine adjuvant, heat-labile enterotoxin from *E. coli* (recombinant or otherwise), cholera toxin, or muramyl dipeptide, among many others. The vaccine can further comprise one or more other immunomodulatory agents such as, e.g., interleukins, interferons, or other cytokines. Vaccines will generally be designed for parenteral administration, although the present invention is compatible with other forms of administration as well, such as e.g., by oral, intranasal, intramuscular, intra-lymph node, intradermal, intraperitoneal, subcutaneous, rectal or vaginal administration, or by a combination of routes. The skilled artisan will readily be able to formulate the vaccine composition according to the route chosen.

Immunization procedures can be optimized using procedures well known in the art. A single dose can be administered to animals, or, alternatively, two or more inoculations can take place with vaccine separated by intervals of two to ten weeks. If desired, sera can be collected from the inoculated animals and tested for the presence of antibodies to BVD virus.

The terms "induction of an immune response," and the like, are used broadly herein to include the induction of, or increase in, any immune-based response in cattle in response to vaccination, including either an antibody or cell-mediated immune response, or both, that serves to protect the vaccinated animal against BVD virus. The terms "protective immunity," "protective immune response," "protect", and the like, as used herein, are not limited to absolute prevention of bovine viral diarrhea in cattle, or absolute prevention of infection of cattle by BVD virus, but are intended to also refer to any reduction in the degree or rate of infection by the pathogen, or any reduction in the severity of the disease or in any symptom or condition resulting from infection with the pathogen as compared to that occurring in an unvaccinated, infected control animal.

E. DNA Vaccines

References describing vaccines and vaccination procedures that utilize nucleic acids (DNA or mRNA) include U.S. Pat. No. 5,703,055, U.S. Pat. No. 5,580,859, U.S. Pat. No. 5,589,466, International Patent Publication WO 98/35562, and various scientific publications, including Ramsay et al., 1997, Immunol. Cell Biol. 75:360–363; Davis, 1997, Cur. Opinion Biotech. 8:635–640; Manickan et al., 1997, Critical Rev. Immunol. 17:139–154; Robinson, 1997, Vaccine 15(8):785–787; Robinson et al., 1996, AIDS Res. Hum. Retr. 12(5):455–457; Lai and Bennett, 1998, Critical Rev. Immunol. 18:449–484; and Vogel and Sarver, 1995, Clin. Microbiol. Rev. 8(3):406–410, which are incorporated herein by reference. These procedures can be utilized to produce a vaccine against BVD virus in which nucleic acid corresponding to BVDdN1 nucleic acid, or to a similar BVD viral genome that has been attenuated by the inactivation of the $N^{pro}$ protease gene, or a degenerate variant thereof, is administered to cattle. A vector containing these nucleic acid molecules can also be used. Immunogens delivered in this manner typically evoke both a humoral and cell-mediated immune response.

Either DNA or RNA encoding the attenuated BVD viral genome can be used in vaccines. The DNA or RNA molecule can be present in a "naked" form or it can be administered together with an agent facilitating cellular uptake (e.g., liposomes or cationic lipids). The typical route of administration will be intramuscular injection of between about 0.1 and about 5 ml of vaccine. Total polynucleotide in the vaccine should generally be between about 0.1 μg/ml and about 5.0 mg/ml. Polynucleotides can be present as part of a suspension, solution or emulsion, but aqueous carriers are generally preferred. Immunization can be accomplished as the result of a single inoculation or due to multiple inoculations. If desired, sera can be collected from the inoculated animals and tested for the presence of antibodies to BVD virus.

The following examples are illustrative only, and are not intended to limit the scope of the present invention.

EXAMPLES

Example 1

Assays and Experimental Methods

DNA

The infectious full-length clone pVVNADL is shown schematically in FIG. 1A. This plasmid contains a ColE1 replicon derived from pGEM4 (Promega Corp.) and is 14,578 bp in length (Vassilev et al., J. Virol. 71:471–478 (1997)). A T7 RNA polymerase promoter is inserted upstream of the BVD viral genome and this promoter can direct viral RNA synthesis. The sequence of the BVD viral genome was derived from the NADL strain of BVD virus (ATCC VR-534).

Amplification of pVVNADL in E. coli

In general, amplification of the full length pVVNADL clone in E. coli has proven difficult. The deleterious effects of long pestivirus cDNAs and full-length clones during propagation in E. coli have been noted previously (Moormann et al., J. Virol. 70:763–770 (1996); Rugglie et al, J. Virol. 70:3478–3487 (1996)). The stability of pVVNADL was tested in several bacterial hosts including E. coli JM109 (Stratagene); DH5α (GibcoBRL); and STBL2 cells (GibcoBRL). After transformation of plasmid DNA into each of these strains, colony size was monitored and gross plasmid structure was analyzed by restriction mapping. Best results were obtained with STBL2 cells. Transformation of pVVNADL into these cells produced relatively uniform populations of small colonies with no evidence of DNA rearrangement under restricted growth conditions (30° C. for no more than 20 hours) and reasonable DNA yield.

In Vitro Transcription and RNA Transfection

RNA transcripts were synthesized in vitro with T7 RNA polymerase using MEGAscript reagent (Ambion) according to the manufacturer's protocol. The pVVNADL DNA template was linearized with SacII and treated with T4 DNA polymerase to remove the 3' overhang. Transcription reaction products were analyzed by gel electrophoresis. 1 to 5 μg of transcript RNA was added to 200 μl of Opti-MEM (GibcoBRL) containing 6 μg of Lipofectin (GibcoBRL) and RNA/lipid samples were incubated for 10 to 15 minutes at room temperature. During this time, MDBK (a derivative of Madin Darby bovine kidney cells (clone 6)) or RD (a stable transformed bovine testis cell line) monolayers (50 to 60% confluent) grown in 6 well plates (35 mm diameter), were washed twice with RNase-free PBS and once with Opti-MEM. After the final wash, the transfection mixtures were added to each well, which were then incubated for 10 minutes at room temperature with gentle rocking. The wells then received 1 ml Opti-MEM and were incubated for another 3 hours at 37° C. A 3 ml volume of Opti-MEM containing 5% fetal equine serum (for RD cells) or fetal bovine serum (for MDBK cells) was added to each well. Following incubation for 1 to 4 days at 37° C., the cells were fixed with 80% acetone and immunohistochemistry assays were performed to help visualize the BVD virus plaques.

Example 2

Construction of $N^{pro}$ Gene-Deleted BVD Viral Clone

In order to generate a BVD virus with the $N^{pro}$ gene deleted from its genome, three DNA fragments were first generated and then ligated together. The exact procedure is described below.

Generation of PCR Fragment I

"PCR Fragment I" was designed to contain a deletion of the coding sequence of $N^{pro}$. Three PCR amplifications were involved in generating this fragment. In the first, the primers 5NTR3(+) and 5NTR4(−) were used to amplify the half of the 5'NTR region upstream of the N$^{pro}$ coding sequence. The 5' positive sense primer 5NTR3(+) had the sequence: 5'-AAAGGTCTCGAGATGCCACG-3' (oligonucleotide 218–237, SEQ ID NO: 2). The 3' negative sense primer 5NTR4(−) had the sequence: 5'-GTCTGACATGTGCCA-TGTACAGCAGAGATTTTTAGTAGC-3' (oligonucleotide 895–890+ 388–356, SEQ ID NO: 3). Both primers are located in the 5'NTR region of the viral genome and the primer 5NTR3(+) contains a unique restriction enzyme site XhoI. Primer 5NTR4(−) contains six extra oligonucleotides at its 5' end which are homologous to the 5' end of the coding sequence of the BVD virus C protein. PCR amplification was performed using primers at a final concentration of 0.5 μM, 10 ng of plasmid pVVNADL DNA as template, and 2.5 units of Pfu DNA polymerase (Stratagene, La Jolla, Calif.). Twenty cycles of amplification were performed using the following conditions: denaturation at 94° C. for 30 seconds; annealing at 55° C. for one minute; and extension at 72° C. for two minutes. After purification by agarose gel electrophoresis, the resulting 177 base pair fragment (fragment A) was resuspended in TE buffer.

A second PCR amplification was performed using the oligonucleotides NADLC6(+) and Seq23(−) as primers for amplifying a fragment downstream of the N$^{pro}$ coding sequence. The 5' positive sense primer NADLC6(+) had the sequence: 5'-CACATGTCAGACACGAAAG AAGAGGGAGC-3' (oligonucleotides 383–388 + 890–913, SEQ ID NO: 4). The 3' negative sense primer Seq23(−) had the sequence: 5'-CAGGTTTGCAATCCAAGTGCCC-3' (oligonucleotide 2480–2459, SEQ ID NO: 5). Primer NADLC6 is located at the N-terminal of protein C. It contains three extra nucleotides homologous to the 3' end of the 5' NTR and an initiation codon, ATG, is located at its 5' end. Primer Seq23(−) is located near the N-terminal of protein E2. The plasmid pVVNADL was used as template in the amplification reaction and the conditions were the same as those described above. The resulting DNA fragment (fragment B) was purified by agarose gel electrophoresis and had a size of 1596 bp.

The third amplification was performed using oligonucleotides 5' NTR3(+) (SEQ ID NO: 2) and Seq23(−) (SEQ ID NO: 5) as primers at a concentration of 0.5 μM, fragments A and B as templates (0.5 μg), and 2.5 units of Pfu DNA polymerase (Stratagene, La Jolla, Calif.). For the first four cycles of amplification, conditions were: denaturation at 94° C. for 30 seconds; annealing at 40° C. for one minute; and extension at 72° C. for two minutes. This was followed by 20 cycles in which conditions were: denaturation at 94° C. for 30 seconds; annealing at 60° C. for one minute; and extension at 72° C. for two minutes. This produced the final product, designated as "PCR Fragment I," with a size of 1767 bp. This fragment was digested with XhoI and PvuI to form a fragment of 1175 bp before being used for ligation.

Generation of PCR Fragment II

"PCR Fragment II" was generated using the oligonucleotides Seq2(+) and Seq24(−) as primers. The sequence of the 5' positive sense primer Seq2(+) is as follows: 5'-GGAGCAT ACGCTGCTTCCCC-3' (oligonucleotide 1865–1884, SEQ ID NO: 6). The 3'—sense primer Seq24(−) had the sequence: 5'-GCCTTGCCTATGAGGGAATGG-3' (oligonucleotide 2963–2942, SEQ ID NO: 7). Oligonucleotide Seq2(+) is located near the N-terminal of E1 and oligonucleotide Seq24(−) is located near the middle of the E2 region. Amplification was performed using the plasmid pVVNADL DNA as template under conditions as described above in connection with the amplification using fragments A and B. The resulting fragment, designated as "PCR Fragment II," had a size of 1098 bp. It was digested with PvuI and RsrII to form a fragment 929 bp in length before being used for ligation.

Generation of Vector Fragment III

The 14579 bp plasmid pVVNADL was digested with XhoI and RsrII to yield a fragment 11974 bp in length. This was given the designation "Vector Fragment III."

Generation of Plasmid pBVDdN1

PCR Fragments I and II and Vector Fragment III were mixed together at a molecular ratio of 2:2:1 and ligated with 200 units of T4 DNA ligase (Boehringer Mannheim) overnight at 16° C. The ligaton product was then transformed into E. coli STBL2 cells and heterologous colonies were screened by mini-DNA purification and specific restriction enzyme digestion. Plasmids having the expected size (14079 bp) were further analyzed by sequence analysis. The resulting plasmid pBVDdN1 is shown in FIG. 1B and contains the expected deletion of the N$^{pro}$ protease gene from BVD viral genome. The vector background for pBVDdN1 is the same as that for pVVNADL.

Example 3

Characterization of N$^{pro}$ Gene-Deleted BVD Viral Clone

Infectivity of the N$^{pro}$ Gene-Deleted BVD Viral Clone pBVDdN1

RNA from pBVDdN1 and pVVNADL (positive control) was synthesized in vitro as described previously, and RNA transfection was performed using Lipofectin on RD cell monolayers. At 48, 72 and 96 hours post-transfection, supernatant was collected from the transfected cells and used to reinfect fresh RD monolayers. The transfected cells were fixed with 80% acetone and then examined in an immunohistochemistry assay performed using a Vectastain Elite ABC kit (Vector Laboratories). Monoclonal antibodies used for detecting BVD-specific viral proteins were 15C5 (specific for E0 )and CA3 (specific for E2) (Pfizer in-house), although other monoclonal antibodies raised against these antigens can be prepared by standard techniques and used in these same procedures. These antibodies were used at a dilution of 1:1000. Envelope proteins E0 and E2 were detected and virus was produced at 24 hours post-transfection with RNA derived from the parental virus. In contrast, the viral proteins E0 and E2 were first detected at 48 hours post-transfection in cells treated with RNA derived from pBVDdN1. BVDdN1 virus was not rescued until 72 hours post-transfection.

Phenotype Analysis

Early passage BVDdN1 virus stocks (passage 3) were used to inoculate RD and MDBK cell monolayers. These cells were compared with controls inoculated with the parental virus. The cell monolayers were fixed with 80% acetone at 20 hours post-transfection (RD cells) or 24 hours post-transfection (MDBK cells). Fixed cells were then analyzed by immunohistochemistry with the E2-specific monoclonal antibody CA3 at a 1:1000 dilution and examined microscopically. It was found for both cell types that the rate of parental virus replication was significantly faster than the rate of replication exhibited by the BVDdN1 virus.

Genotype Analysis

RNA of both parental virus and BVDdN1 (passage 3) was purified from infected RD monolayers using the Ultraspec™ RNA reagent (Biotect) following the manufacturer's instructions. RT/PCR experiments were performed using RT-PCR beads (Pharmacia Biotech) and the oligonucleotides NADLE07(−) and 5NTR3(+). The sequence and location of the 5NTR3(+) oligonucleotide has been described above.

The sequence of oligonucleotide NADLE07(-) is as follows: 5'-CACTTGCATCCATCATACC-3' (negative sense, oligonucleotide 1379–1361, SEQ ID NO: 8). This oligonucleotide is located approximately 150 bp from the N-terminal of E0. It was found that RT/PCR from parental RNA yielded a fragment 1162 bp in size. RT/PCR from BVDdN1 RNA yielded a fragment 661 bp in size, which is as expected for a fragment that had deleted the $N^{pro}$ protease gene. The RT/PCR fragments generated from both parental and BVDdN1 RNAs were sequenced. In both cases, the sequence obtained was as expected and corresponded to the arrangement of elements shown in FIG. 1. The complete sequence of BVDdN1 is shown in SEQ ID NO: 1 from nt 39 to nt 12116.

Example 4

BVDdN1 Efficacy Study

The purpose of the present study was to evaluate the ability of a vaccine comprising BVDdN1 to cause seroconversion in calves. Fifteen animals (10 for two-dose vaccination with 5 sentinels) were randomly assigned to a first room. Ten other animals were randomly assigned to a second room (one-dose vaccination, no sentinels). BVDdN1 virus was administered to the animals subcutaneously at a dose of $10^7$ $TCID_{50}$/animal in 2.0 ml MDBK cell lysate. On the days of immunization, the 5 designated sentinel animals were removed from their room. The remaining 10 calves were vaccinated with BVDdN1 virus. Approximately 24 hours post-immunization, the sentinel animals were returned to the treatment room. A second vaccine dose was administered to the first 10 animals in a similar manner approximately 28 days following the first dose.

Rectal temperatures were taken on days -1, 0 (prior to vaccination), 1, 2, 3, 4, 5, 6, 7, 8, 9, 10 (all groups), and on days 27, 28 29, 30, 31, 32, 33, 34, 35, 36, 37 and 38 (for animals in the 2-dose group). Blood samples were collected from animals in the 2-dose group on day 0 and weekly thereafter (i.e., on days 7, 14, 21, 28, 35, 42, 49, 56, 63, 70, 77, 84 and 91). Blood samples were collected from animals in the 1-dose group on days 0, 7, 14, 21, 28, 35, 42, 49, 56 and 63.

Serum neutralizing antibodies were detected by SN assay (using BVD virus isolate 5960 for type I, and isolate 890 for type II) to monitor anticipated homologous and heterologous protection.

No significant variations were observed for either general observations or rectal temperatures. None of the sentinel animals seroconverted during the course of the study (data not shown).

Figure 3A:
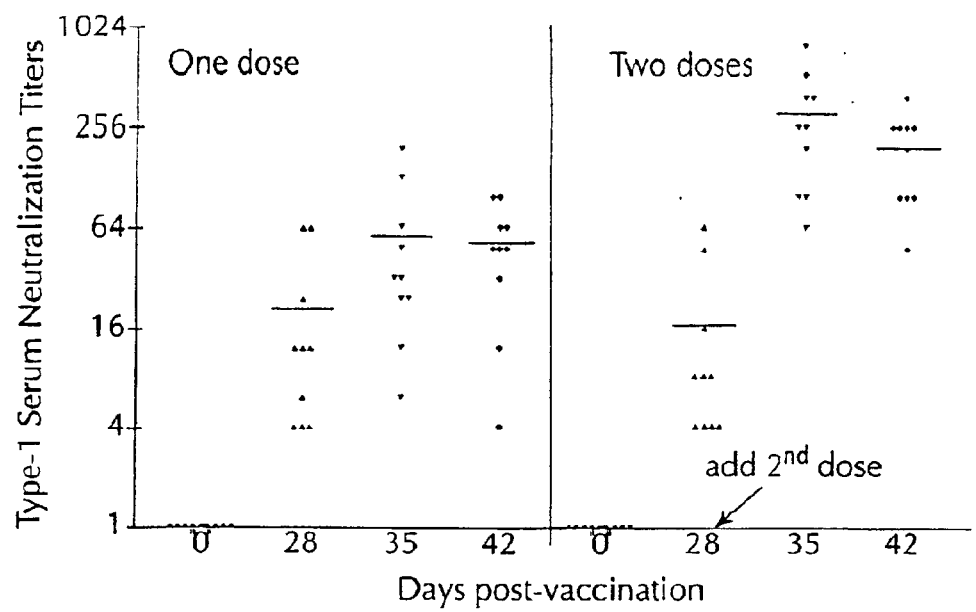
FIG. 3. Data demonstrating seroconversion in cattle in response to administration of BVDdN1 virus.
Figure 3B:
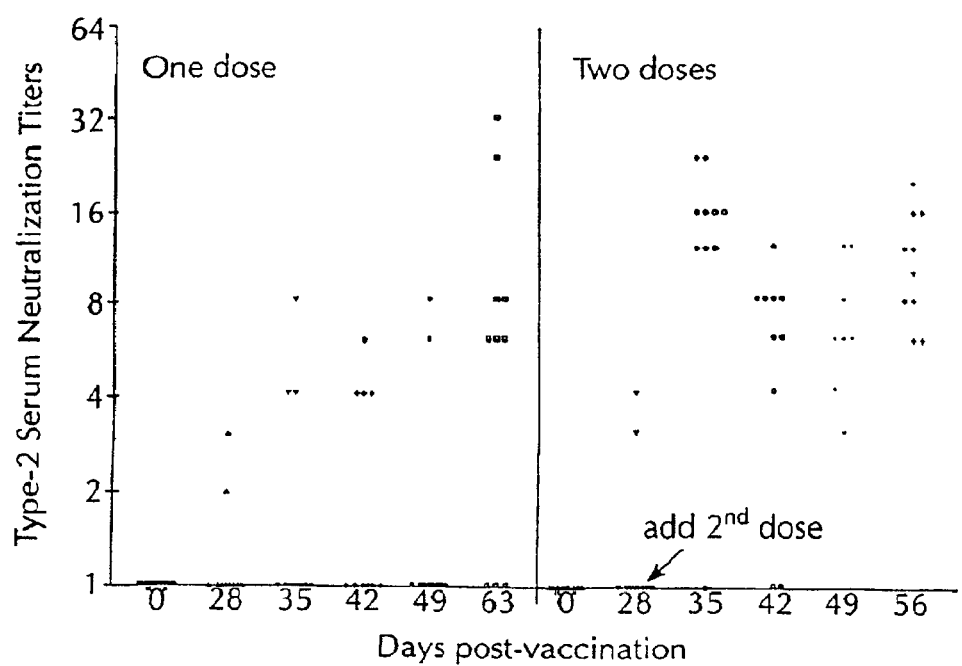

All BVDdN1 virus-vaccinated animals seroconverted, as determined by the type I serum neutralization assay. After a single dose vaccination, 60% of the animals reached a positive titer of 1:8 or higher at 28 days; and 90% of the animals reached a positive tier of 1:8 or higher at day 35, and subsequently retained a high titer (FIG. 3A). In the type II serum neutralization assay, 70% of the animals were positive at day 63 post-vaccination (data not shown). After a two-dose vaccination, all of the animals reached a positive titer of 1:64 or higher at 7 days, as shown by type I serum neutralization assay, and subsequently maintained a similar seroconversion level (FIG. 3A). For type II serum neutralization assay, most of the animals had a positive titer at 7 days post-second vaccination, and at least 60% of the animals reached a positive titer of 1:8 or above at day 28 (FIG. 3B). These results indicate that BVDdN1 virus is able to replicate in cattle and induce a positive neutralization serum for both type-1 and type-2 viruses, which supports the use of this virus as a vaccinal agent for BVDV prevention.

Deposit of Biological Materials

Plasmid pBVDdN1 was deposited with the American Type Culture Collection (ATCC) at 10801 University Blvd, Manassas, Va., 20110, U.S.A., on Oct. 20, 1998, and was assigned accession number ATCC 203354.

All patents, patent applications, and publications cited above are incorporated herein by reference in their entirety.

The present invention is not limited in scope by the specific embodiments described, which are intended as single illustrations of individual aspects of the invention. Functionally equivalent compositions and methods are within the scope of the invention. Indeed, various modifications of the invention, in addition to those shown and described herein, will become apparent to those skilled in the art from the foregoing description. Such modifications are intended to fall within the scope of the appended claims.

What is claimed is:

1. An attenuated, bovine viral diarrhea (BVD) virus, wherein said virus has a genomic nucleic acid sequence comprising the sequence of SEQ ID NO:1 from nt 39 to nt 12116 or a degenerate variant thereof, wherein said degenerate variant encodes the same amino acid sequence encoded by SEQ ID No: 1 from nt39to nt 12116.

2. The attenuated BVD virus of claim 1, wherein said virus has a genomic nucleic acid sequence consisting essentially of the sequence of SEQ ID NO:1 from nt 39 to nt 12116 or a degenerate variant thereof, wherein said degenerate variant encodes the same amino acid sequence encoded by SEQ ID No: 1 from nt 39 to nt 12116.

3. The virus of claim 1, in substantially purified form.

4. A host cell infected with the virus of claim 1.

5. An attenuated BVD progeny virus produced by the host cell of claim 4.

6. An attenuated BVD progeny virus produced by a host cell transformed or transfected with the nucleic acid molecule of SEQ ID NO: 1 from nt 39 to nt 12116.

7. A method of inducing an immune response in cattle, comprising administering the virus of claim 1 to said cattle at a dosage sufficient to induce protective immunity against subsequent infection with BVD virus.

8. The method of claim 7, wherein the protective immunity results from both a humoral and cell-mediated immune response.

9. A method of inducing the production of antibody to BVD virus in an animal capable of making antibody, comprising administering the virus of claim 1 to said animal at a dosage effective to induce said production of antibody.

10. The method of claim 9, wherein said antibody is produced in cattle.

11. The method of claim 9, further comprising isolating said antibody from said animal.

* * * * *